(12) United States Patent
Selkirk et al.

(10) Patent No.: US 8,704,037 B2
(45) Date of Patent: Apr. 22, 2014

(54) TARGETED CELL DEATH

(75) Inventors: Stephen M. Selkirk, Mayfield, OH (US); Robert H. Miller, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 34 days.

(21) Appl. No.: 13/374,307

(22) Filed: Dec. 21, 2011

(65) Prior Publication Data

US 2012/0198574 A1 Aug. 2, 2012

Related U.S. Application Data

(62) Division of application No. 12/138,277, filed on Jun. 12, 2008, now Pat. No. 8,124,749.

(60) Provisional application No. 60/943,448, filed on Jun. 12, 2007.

(51) Int. Cl.
*G01N 33/483* (2006.01)
*G01N 33/566* (2006.01)
*A01K 67/027* (2006.01)
*C12Q 1/68* (2006.01)
*G06F 19/00* (2011.01)

(52) U.S. Cl.
USPC ..... 800/3; 800/13; 800/14; 800/18; 435/61.3; 435/79.2; 436/501; 702/19

(58) Field of Classification Search
None
See application file for complete search history.

(56) References Cited

U.S. PATENT DOCUMENTS

| | | | |
|---|---|---|---|
| 4,873,191 A | 10/1989 | Wagner et al. |
| 5,002,753 A | 3/1991 | Zeicher et al. |
| 5,175,384 A | 12/1992 | Krimpenfort et al. |
| 5,175,385 A | 12/1992 | Wagner et al. |
| 5,298,429 A | 3/1994 | Evans et al. |
| 5,464,758 A | 11/1995 | Gossen et al. |
| 5,534,418 A | 7/1996 | Evans et al. |
| 5,589,362 A | 12/1996 | Bujard et al. |
| 5,650,298 A | 7/1997 | Bujard et al. |
| 6,172,190 B1 | 1/2001 | Hunter et al. |
| 6,235,872 B1 | 5/2001 | Bredesen et al. |
| 6,245,330 B1 | 6/2001 | Horellou et al. |
| 6,313,373 B1 | 11/2001 | Eckert et al. |
| 6,472,520 B2 | 10/2002 | Fisher |
| 6,656,971 B2 | 12/2003 | Wu et al. |
| 6,677,311 B1 | 1/2004 | Evans et al. |
| 6,753,456 B2 | 6/2004 | Lester et al. |
| 6,781,029 B2 | 8/2004 | Nilsson et al. |
| 6,839,586 B2 | 1/2005 | Webb |
| 6,881,555 B2 | 4/2005 | Guo et al. |
| 6,890,726 B1 | 5/2005 | Sauer et al. |
| 6,891,081 B1 | 5/2005 | Stern et al. |
| 6,903,244 B1 | 6/2005 | Keating et al. |
| 6,905,823 B2 | 6/2005 | Kallioniemi et al. |
| 6,909,031 B2 | 6/2005 | Allen et al. |
| 6,977,733 B2 | 12/2005 | Denk et al. |
| 6,982,082 B1 | 1/2006 | Schreiber et al. |
| 6,984,635 B1 | 1/2006 | Schreiber et al. |
| 7,022,319 B1 | 4/2006 | Gunzburg et al. |
| 7,033,595 B1 | 4/2006 | Sanders et al. |
| 7,101,357 B2 | 9/2006 | Tanaka et al. |
| 7,109,317 B1 | 9/2006 | Clemons et al. |
| 7,153,685 B2 | 12/2006 | Mao et al. |
| 7,169,564 B1 | 1/2007 | Du et al. |
| 7,196,182 B2 | 3/2007 | Reed et al. |
| 8,124,749 B2 | 2/2012 | Selkirk et al. |
| 2003/0110524 A1 | 6/2003 | Stringer |
| 2003/0199022 A1 | 10/2003 | Mao et al. |
| 2005/0187177 A1 | 8/2005 | Godbey et al. |
| 2006/0030541 A1 | 2/2006 | Garcia et al. |
| 2006/0034767 A1 | 2/2006 | Lum et al. |
| 2006/0035269 A1 | 2/2006 | Hartley et al. |
| 2006/0040386 A1 | 2/2006 | Holgersson |
| 2006/0052327 A1 | 3/2006 | Liu et al. |
| 2006/0193841 A1 | 8/2006 | Mandel et al. |
| 2008/0096202 A1 | 4/2008 | Popko et al. |
| 2009/0010873 A1 | 1/2009 | Elsenback-Schwartz et al. |
| 2009/0019554 A1 | 1/2009 | Selkirk et al. |
| 2010/0299770 A1 | 11/2010 | Selkirk et al. |

FOREIGN PATENT DOCUMENTS

| | | |
|---|---|---|
| WO | WO 2006/108525 A1 | 10/2006 |
| WO | WO 2006/138412 A2 | 12/2006 |
| WO | WO 2006/138412 A3 | 8/2007 |

OTHER PUBLICATIONS

Skoff et al (Neurochemical Research. 2004; 29(11): 2095-2103).*
Taupin et al. (Eur. J. Immunol. 1997; 27: 905-913).*
U.S. Appl. No. 13/393,782, filed Mar. 1, 2012, Popko et al.
Arnett, et al. bHLH transcription factor Olig1 is required to repair demyelinated lesions in the CNS. Science. Dec. 17, 2004;306(5704):2111-5.
Baerwald, et al. Developing and mature oligodendrocytes respond differently to the immune cytokine interferon-gamma. J Neurosci Res. Apr. 15, 1998;52(2):230-9.
Balabanov, et al. Myelin repair: developmental myelination redux? Nat Neurosci. Mar. 2005;8(3):262-4.
Belshaw, et al. Controlling protein association and subcellular localization with a synthetic ligand that induces heterodimerization of proteins. Proc Natl Acad Sci U S A. 1996; 93(10):4604-7.
Brockschnieder, et al. An Improved Mouse Line for Cre-Induced Cell Ablation Due to Diphtheria Toxin A, Expressed From the Rosa26 Locus. Genesis. 2006; 44:322-327.
Brockschnieder, et al. Cell Depletion Due to Diphtheria Toxin Fragment A after Cre-Mediated Recombination. Molecular and Cellular Biology. 2004; p. 7636-7642.
Brockschnieder, et al. Ermin, A Myelinating Oligodendrocyte-Specific Protein That Regulates Cell Morphology. The Journal of Neuroscience. 2006; 26(03):757-762.
Bruck, et al. Remyelination in multiple sclerosis. J Neurol Sci. Feb. 15, 2003;206(2):181-5.

(Continued)

*Primary Examiner* — Scott Long
(74) *Attorney, Agent, or Firm* — Wilson Sonsini Goodrich & Rosati

(57) ABSTRACT

The present invention provides compositions and methods for studying neuropathy. The compositions and methods provided herein are particularly useful for screening agents of therapeutic and/or diagnostic potential.

42 Claims, 11 Drawing Sheets

(56) References Cited

OTHER PUBLICATIONS

Buch, et al. A Cre-inducible diptheria toxin receptor mediates cell lineage ablation after toxin administration. Nature Publishing Group. 2005; vol. 2 No. 6: 419.

Case Western Reserve University. Source Symposium & Poster Session Support of Undergraduate Research and Creative Endeavoers. Apr. 20, 2007, pp. 1-90. Available at www.case.edu/source/symposium/2007AbstractCompendium.pdf. Accessed May 31, 2010. Abstract: Inducible Caspase 9 mediated cell death of oligodendrocytes: A novel model of acute focal demyelination, p. 43.

Chang, et al. NG2-positive oligodendrocyte progenitor cells in adult human brain and multiple sclerosis lesions. J Neurosci. Sep. 1, 2000;20(17):6404-12.

Chen, et al. TiProD: the Tissue-specific Promoter Database. Nucleic Acids Res. Jan. 1, 2006;34(Database issue):D104-7.

Clark, et al. A future for transgenic livestock. Nat Rev Genet. Oct. 2003;4(10):825-33.

Compston, et al. Multiple sclerosis. Lancet. Apr. 6, 2002;359(9313):1221-31.

Contag, et al. Photonic detection of bacterial pathogens in living hosts. Mol Microbiol. Nov. 1995;18(4):593-603.

Cunningham, et al. Analysis of proliferation markers and p53 expression in gliomas of astrocytic origin: relationships and prognostic value. J Neurosurg. Jan. 1997;86(1):121-30.

Doerflinger, et al. Inducible Site-Specific Recombination in Myelinating Cells. Genesis. 2003; 35:63-72.

European search report dated Jun. 28, 2010 for Application No. 08770889.7.

Farhadi, et al. A combinatorial network of evolutionarily conserved myelin basic protein regulatory sequences confers distinct glial-specific phenotypes. J Neurosci. Nov. 12, 2003;23(32):10214-23.

Feil, et al. Ligand-activated site-specific recombination in mice. Proc Natl Acad Sci U S A. Oct. 1, 1996;93(20):10887-90.

Feil, et al. Regulation of Cre recombinase activity by mutated estrogen receptor ligand-binding domains. Biochem Biophys Res Commun. Aug. 28, 1997;237(3):752-7.

Flusberg, et al. Fiber-optic fluorescence imaging. Nat Methods. Dec. 2005;2(12):941-50.

Girard, et al. Grafts of brain-derived neurotrophic factor and neurotrophin 3-transduced primate Schwann cells lead to functional recovery of the demyelinated mouse spinal cord. J Neurosci. Aug. 31, 2005;25(35):7924-33.

Gossen, et al. Tight control of gene expression in mammalian cells by tetracycline-responsive promoters. Proc Natl Acad Sci U S A. Jun. 15, 1992;89(12):5547-51.

Hisahara, et al. Caspase-11 mediates oligodendrocyte cell death and pathogenesis of autoimmune-mediated demyelination. J Exp Med. Jan. 1, 2001;193(1):111-22.

Hisahara, et al. Caspase-mediated oligodendrocyte cell death in the pathogenesis of autoimmune demyelination. Neurosci Res. Aug. 2003;46(4):387-97.

International search report dated Nov. 8, 2010 for PCT Application No. US10/47761.

International search report dated Aug. 20, 2008 for PCT Application No. US2008/66774.

Ivanova, et al. In Vivo Genetic Ablation by Cre-Mediated Expression of Diptheria Toxin Fragment A. UKPMC Funders Group Author Manuscript, Genesis. 2005; 43(3):129-135.

Jalabi, et al. Recovery of Myelin after Induction of Oligodendrocyte Cell Death in Postnatal Brain. The Journal of Neuroscience. 2005; 25(11);2885-2894.

Jung, et al. In vivo mammalian brain imaging using one- and two-photon fluorescence microendoscopy. J Neurophysiol. Nov. 2004;92(5):3121-33. Epub May 5, 2004.

Kellendonk, et al. Inducible site-specific recombination in the brain. J Mol Biol. Jan. 8, 1999;285(1):175-82.

Kirik, et al. Nigrostriatal alpha-synucleinopathy induced by viral vector-mediated overexpression of human alpha-synuclein: a new primate model of Parkinson's disease. Proc Natl Acad Sci U S A. Mar. 4, 2003;100(5):2884-9. Epub Feb. 24, 2003.

Landy. Mechanistic and structural complexity in the site-specific recombination pathways of Int and FLP. Curr Opin Genet Dev. Oct. 1993;3(5):699-707.

Leone, et al. Tamoxifen-inducible glia-specific Cre mice for somatic mutagenesis in oligodendrocytes and Schwann cells. Molecular and Cellular Neuroscience. 2003; 430-440.

Lo. Transformation by iontophoretic microinjection of DNA: multiple integrations without tandem insertions. Mol Cell Biol. Oct. 1983;3(10):1803-14.

Lucchininetti, et al. A quantitative analysis of oligodendrocytes in multiple sclerosis lesions. A study of 113 cases. Brain. Dec. 1999;122 ( Pt 12):2279-95.

Mansfield, et al. Autofluorescence removal, multiplexing, and automated analysis methods for in-vivo fluorescence imaging. J Biomed Opt. Jul.-Aug. 2005;10(4):41207.

Mathis, et al. A Transgenic Mouse Model for Inducible and Reversible Dysmyelination. The Journal of Neuroscience. 2000; 20(20): 7698-7705.

Mehta, et al. Fiber optic in vivo imaging in the mammalian nervous system. Curr Opin Neurobiol. Oct. 2004;14(5):617-28.

Meng, et al. Characterization of an intronic enhancer that regulates myelin proteolipid protein (Plp) gene expression in oligodendrocytes. J Neurosci Res. Nov. 1, 2005;82(3):346-56.

Merrill, et al.. In Vitro and In Vivo Pharmacological Models to Assess Demyelination and Remyelination. Neuropsychopharmacology. 2009;34, 55-73.

Morelli, et al. Neuronal and glial cell type-specific promoters within adenovirus recombinants restrict the expression of the apoptosis-inducing molecule Fas ligand to predetermined brain cell types, and abolish peripheral liver toxicity. Journal of General Virology. 1999; 80:571-583.

Mukouyama, et al. Olig2+ neuroepithelial motoneuron progenitors are not multipotent stem cells in vivo. Proc Natl Acad Sci U S A. Jan. 31, 2006;103(5):1551-6. Epub Jan. 23, 2006.

Nor, et al. Ablation of microvessels in vivo upon dimerization of iCaspase-9. Gene Ther. Apr. 2002;9(7):444-51.

Patterson, et al. Cloning and functional analysis of the promoter for KDR/flk-1, a receptor for vascular endothelial growth factor. J Biol Chem. Sep. 29, 1995;270(39):23111-8.

Rivera-Quinones, et al. Absence of neurological deficits following extensive demyelination in a class I-deficient murine model of multiple sclerosis. Nat Med. Feb. 1998;4(2):187-93.

Ruffini, et al. Distinctive properties of human adult brain-derived myelin progenitor cells. Am J Pathol. Dec. 2004;165(6):2167-75.

Sauer. Site-specific recombination: developments and applications. Curr Opin Biotechnol. Oct. 1994;5(5):521-7.

Scahill, et al. Expression and characterization of the product of a human immune interferon cDNA gene in Chinese hamster ovary cells. Proc Natl Acad Sci U S A. Aug. 1983;80(15):4654-8.

Schindehutte, et al. In vivo and in vitro tissue-specific expression of green fluorescent protein using the cre-lox system in mouse embryonic stem cells. Stem Cells. 2005;23(1):10-5.

Shinoura, et al. Adenovirus-mediated overexpression of Fas induces apoptosis of gliomas. Cancer Gene Ther. Feb. 2000;7(2):224-32.

Shinoura, et al. Adenovirus-mediated transfer of bax with caspase-8 controlled by myelin basic protein promoter exerts an enhanced cytotoxic effect in gliomas. Cancer Gene Ther. May 2000;7(5):739-48.

Shinoura, et al. Adenovirus-mediated transfer of caspase-8 augments cell death in gliomas: implication for gene therapy. Hum Gene Ther. May 20, 2000;11(8):1123-37.

Shinoura, et al. Adenovirus-mediated transfer of p33ING1 with p53 drastically augments apoptosis in gliomas. Cancer Res. Nov. 1, 1999;59(21):5521-8.

Southern, et al. Transformation of mammalian cells to antibiotic resistance with a bacterial gene under control of the SV40 early region promoter. J Mol Appl Genet. 1982;1(4):327-41.

Springer. Apoptotic cell death following traumatic injury to the central nervous system. J Biochem Mol Biol. Jan. 31, 2002;35(1):94-105.

(56) References Cited

OTHER PUBLICATIONS

Stidworthy, et al. Notch1 and Jagged1 are expressed after CNS demyelination, but are not a major rate-determining factor during remyelination. Brain. Sep. 2004;127(Pt 9):1928-41. Epub Aug. 2, 2004.

Straathof, et al. An inducible caspase 9 safety switch for T-cell therapy. Blood. 2005; 105(11):4247-54.

Subramini, et al. Expression of the mouse dihydrofolate reductase complementary deoxyribonucleic acid in simian virus 40 vectors. Mol Cell Biol. Sep. 1981;1(9):854-64.

Urlaub, et al. Isolation of Chinese hamster cell mutants deficient in dihydrofolate reductase activity. Proc Natl Acad Sci U S A. Jul. 1980;77(7):4216-20.

Van Der Putten, et al. Efficient insertion of genes into the mouse germ line via retroviral vectors. Proc Natl Acad Sci U S A. Sep. 1985;82(18):6148-52.

Vanderluit, et al. Model for Focal Demyelination of the Spinal Dorsal Columns of Transgenic MBP-LacZ Mice by Phototargeted Ablation of Oligodendrocytes. Journal of Neuroscience Research. 2000; 62:28-39.

Woski, et al. Oligodendrocyte injury in multiple sclerosis: a role for p53. Journal of Neurochemistry. 2003; 85:635-644.

Wu, et al. Caspase 9 is required for p53-dependent apoptosis and chemosensitivity in a human ovarian cancer cell line. Oncogene. Jan. 3, 2002;21(1):1-8.

Wu, et al. Receptor-mediated in vitro gene transformation by a soluble DNA carrier system. J Biol Chem. Apr. 5, 1987;262(10):4429-32.

Zhang, et al. A transgenic mouse model with a luciferase reporter for studying in vivo transcriptional regulation of the human CYP3A4 gene. Drug Metab Dispos. Aug. 2003;31(8):1054-64.

Bharucha, et al. Characterization of the cis-acting elements of the mouse myelin P2 promoter. J Neurosci Res. Dec. 1, 1993;36(5):508-19.

Gravel, et al. Four-kilobase sequence of the mouse CNP gene directs spatial and temporal expression of lacZ in transgenic mice. J Neurosci Res. Aug. 15, 1998;53(4):393-404.

Maier, et al. Distinct elements of the peripheral myelin protein 22 (PMP22) promoter regulate expression in Schwann cells and sensory neurons. Mol Cell Neurosci. Nov. 2003;24(3):803-17.

Mallon, et al. Proteolipid promoter activity distinguishes two populations of NG2-positive cells throughout neonatal cortical development. J Neurosci. Feb. 1, 2002;22(3):876-85.

Scherer, et al. Transgenic expression of human connexin32 in myelinating Schwann cells prevents demyelination in connexin32-null mice. J Neurosci. Feb. 9, 2005;25(6):1550-9.

Yonemasu, et al. Proximal promoter region is sufficient to regulate tissue-specific expression of UDP-galactose: ceramide galactosyltransferase gene. J Neurosci Res. Jun. 15, 1998;52(6):757-65.

Zhang, et al. Specific expression in mouse mesoderm- and neural crest-derived tissues of a human PDGFRA promoter/lacZ transgene. Mech Dev. Jan. 1998;70(1-2):167-80.

Office action dated May 23, 2012 for U.S. Appl. No. 12/664,387.

Probert, et al. Spontaneous inflammatory demyelinating disease in transgenic mice showing central nervous system-specific expression of tumor necrosis factor alpha. Proc Natl Acad Sci U S A. Nov. 21, 1995;92(24):11294-8.

Hammer, et al. Spontaneous inflammatory disease in transgenic rats expressing HLA-B27 and human beta 2m: an animal model of HLA-B27-associated human disorders. Cell. Nov. 30, 1990; 63(5):1099-112.

Hayashi, et at. Efficient recombination in diverse tissues by a tamoxifen-inducible form of Cre: a tool for temporally regulated gene activation/inactivation in the mouse. Dev Biol. Apr. 15, 2002; 244(2):305-18.

Mullins, et al. Expression of the DBA/2J Ren-2 gene in the adrenal gland of transgenic mice. EMBO J. Dec. 20, 1989; 8(13):4065-72.

Mullins, et al. Fulminant hypertension in transgenic rats harbouring the mouse Ren-2 gene. Nature. Apr. 5, 1990; 344(6266):541-4.

Niemann, et al. Transgenic farm animals: present and future. Rev Sci Tech. Apr. 2005; 24(1):285-98.

Office action dated Apr. 24, 2013 for U.S. Appl. No. 13/393,782.

Prelle, et al. Pluripotent stem cells—model of embryonic development, tool for gene targeting, and basis of cell therapy. Anat Histol Embryol. Jun. 2002; 31(3):169-86.

Qi, et al. A new transgenic rat model of hepatic steatosis and the metabolic syndrome. Hypertension. May 2005; 45(5):1004-11. Epub Apr. 4, 2005.

Ristevski, S. Making better transgenic models: conditional, temporal, and spatial approaches. Mol Biotechnol. Feb. 2005; 29(2):153-63.

Smith, K.R. Gene transfer in higher animals: theoretical considerations and key concepts. J Biotechnol. Oct. 9, 2002; 99(1):1-22.

Taurog, et al. HLA-B27 in inbred and non-inbred transgenic mice. Cell surface expression and recognition as an alloantigen in the absence of human beta 2-microglobulin. J Immunol. Dec. 1, 1988; 141(11):4020-3.

\* cited by examiner

TARGETED CELL DEATH

CROSS REFERENCE

This application claims priority under 35 USC 120 as a divisional application of U.S. Ser. No. 12/138,277, filed Jun. 12, 2008, which claims the benefit under 35 USC 119(e) of U.S. Provisional Application No. 60/943,448, filed Jun. 12, 2007, both of which are incorporated herein by reference in their entirety.

SEQUENCE LISTING

The instant application contains a Sequence Listing which has been submitted via EFS-Web and is hereby incorporated by reference in its entirety. Said ASCII copy, created on Apr. 2, 2012, is named 28890-711-401-Sequencelisting.txt and is 736 bytes in size.

BACKGROUND OF THE INVENTION

Neuronal demyelination is a deleterious condition characterized by a reduction of myelin in the nervous system. Vital to both of the central (CNS) and peripheral (PNS) nervous system, myelin encases the axons of neurons and forms an insulating layer known as the myelin sheath. The presence of the myelin sheath enhances the speed and integrity of nerve signal in form of electric potential propagating down the neural axon. The loss of myelin sheath produces significant impairment in sensory, motor and other types of functioning as nerve signals reach their targets either too slowly, asynchronously (for example, when some axons in a nerve conduct faster than others), intermittently (for example, when conduction is impaired only at high frequencies), or not at all.

Neuronal tissue generally comprises neurons and supporting glial cells. Glial cells outnumber neurons by about ten to one in the mammalian brain. Glial cells may be divided into four types: astrocytes, oligodendrocytes, Schwann cells and microglial cells. The myelin sheath is formed by the plasma membrane, or plasmalemma, of glial cells—oligodendrocytes in the CNS, and Schwann cells in the PNS. During the active phase of myelination, each oligodendrocyte in the CNS typically produce as much as approximately 5000 $\mu m^2$ of myelin surface area per day and approximately $10^5$ myelin protein molecules per minute (Pfeiffer et al. (1993) *Trends Cell Biol.* 3: 191-197). Myelinating oligodendrocytes have been identified at demyelinated lesions, indicating that demyelinated axons may be repaired with the newly synthesized myelin.

Neuronal demyelination is manifested in a large number of hereditary and acquired disorders of the CNS and PNS. These disorders include, for example, Multiple Sclerosis (MS), Progressive Multifocal Leukoencephalopathy (PML), Encephalomyelitis, Central Pontine Myelolysis (CPM), Anti-MAG Disease, Leukodystrophies: Adrenoleukodystrophy (ALD), Alexander's Disease, Canavan Disease, Krabbe Disease, Metachromatic Leukodystrophy (MLD), Pelizaeus-Merzbacher Disease, Refsum Disease, Cockayne Syndrome, Van der Knapp Syndrome, and Zellweger Syndrome, Guillain-Barre Syndrome (GBS), chronic inflammatory demyelinating polyneuropathy (CIDP), and multifocal motor neuropathy (MMN). For the vast majority of these disorders, there are no cures and few effective therapies.

During Parkinsons's disease (paralysis agitans or shaking palsy) cells of the brain appear to deteriorate for unknown reasons. However, a role for inflammatory reactions has been postulated to play a role in the pathogenesis of Parkinson's. Parkinson's is a disorder of the brain characterized by shaking and difficulty with walking, movement, and coordination. The disease affects approximately 2 out of 1,000 people, and most often develops after age 50. It affects both men and women and is one of the most common neurologic disorders of the elderly. Parkinson's disease is caused by progressive deterioration of the nerve cells of the part of the brain that controls muscle movement (the basal ganglia and the extrapyramidal area).

In addition to the loss of muscle control, some people with Parkinson's disease become severely depressed. Although early loss of mental capacities is uncommon, with severe Parkinson's the person may exhibit overall mental deterioration (including dementia, hallucinations, and so on). Dementia can also be a side effect of some of the medications used to treat the disorder.

Amyotrophic Lateral Sclerosis (ALS) is a rapidly progressive, invariably fatal, disorder causing loss of nervous control of voluntary muscles because of destruction of nerve cells in the brain and spinal cord resulting in loss of the use and control of muscles. The nerves controlling these muscles shrink and disappear, which results in loss of muscle tissue due to the lack of nervous stimulation. Muscle strength and coordination decreases, beginning with the voluntary muscles (e.g., those under conscious control). The extent of loss of muscle control continues to progress, and more muscle groups become involved. There may be a loss of nervous stimulation to semi-voluntary muscles, such as the muscles that control breathing and swallowing. Eventually, all muscles under voluntary control are affected, and patients lose their strength and the ability to move their arms, legs, and body.

Motor neurons located in the brain, brainstem, and spinal cord serve as controlling units and vital communication links between the nervous system and the voluntary muscles of the body. Messages from motor neurons in the brain (upper motor neurons) are transmitted to motor neurons in the spinal cord (lower motor neurons) and from them to particular muscles. In ALS, both the upper motor neurons and the lower motor neurons degenerate or die, ceasing to send messages to muscles. Unable to function, the muscles gradually weaken, waste away (atrophy), and twitch (fasciculations). Eventually, the ability of the brain to start and control voluntary movement is lost. The cause is unknown.

MS is the leading cause of nontraumatic CNS morbidity in young adults. The young age of onset and progressive nature of the disease imposes an enormous economic and social burden on society. Acute exacerbations in typical relapsing-remitting MS are the manifestation of acute and focal inflammation and demyelination in the CNS and have long been considered the primary pathology of MS. These events are the target of currently approved therapeutic agents. However, correlations of $T_2$ inflammatory signal on magnetic resonance (MR) images and disease progression are weak as are the clinical characteristics during the relapsing-remitting (RR) phase and subsequent progression of disability. Furthermore, once irreversible disability is reached, the progression to further disability is not affected by relapses, including those occurring before or after the onset of irreversible injury.

In addition to permanent neurological disability due to axonal loss, inflammatory demyelination plays a role in MS pathogenesis. In contrast to inflammation, axonal loss typically correlates with T1 black holes, decreased N-acetyl aspartate (NAA) on magnetic resonance spectroscopy (MRS) and the degree of spinal cord atrophy, which can correlate with clinical disability in patients. These changes have been noted in patients as early as six months after diagnosis, but in most patients the chronic, and perhaps global, axonal injury breaches a clinical threshold at the onset of the secondary progressive phase of the disease.

During the acute inflammatory stage of the disease (clinically defined as relapsing/remitting MS, or RRMS), inflammatory mediators likely contribute to axonal injury. Associations have been made between the number of CD8+ T cells and the extent of axonal damage and animal models tend to support this implicating a CD8-MHC class I pathway of axon destruction (Rivera-Quinones et al., (1998) *Nat. Med.* 4:187-193). Further support comes from pathology studies in which activated CD8 T cells containing cytotoxic granules polarized toward the demyelinated axons suggests direct CD8+ T cell toxicity. Macrophages and microglial cells have been found in close proximity to degenerating axons. These cell types play a role in the homeostatic mechanism of removing debris from the CNS, however they also release inflammatory mediators including proteases, cytokines and free radicals such as nitrous oxide (NO). Finally, antibodies and complement may also play a role in axon damage during acute inflammation. Levels of anti-ganglioside antibodies were found to be significantly higher in primary progressive MS (PPMS) than in secondary progressive or RRMS and axons exposed to complement after demyelination may activate the complement cascade directly.

The relationship between inflammation and neuron loss in MS has not been fully delineated. There is a need to establish a model of oligodendrocyte loss and subsequent demyelination that does not rely on the induction of inflammation to specific CNS antigens systemically or necessitate the use of a potent system adjuvant. Such a model that utilizes antigens and inflammation typically fails to recapitulate demyelination and neuronal loss identified in MS patients.

An accurate animal model of axonal transection and neuronal loss should mimic the pathological features identified in MS brain specimens. This includes the identification of transected axons, transected dendrites and neuronal apoptosis in acute cortical lesions. The acute event should also result in measurable impaired neurotransmission that is restored, to varying degrees, by the redistribution of $Na^+$ channels as has been identified in MS pathology specimens. Chronic lesions should demonstrate a variable degree of remyelination and smoldering persistent axonal loss should be evident. Finally, neuron loss in the animal model should be identified in regions anatomically distinct and temporally distinct from original demyelinating lesions mimicking the effect of the disease on NAWM. These features would provide an important and accurate depiction of the effects on neurons identified in pathology specimens from MS patients.

The delineation of the precise molecular mechanism and pathogenesis of neuropathy and in particular neuronal demyelination, has been hampered by the continued lack of effective animal models. Thus, there remains a pressing need for composition and methods to effect a robust screen for therapeutics directed to neuronal disorders.

SUMMARY OF THE INVENTION

The present invention provides compositions and methods for understanding the process of neuropathy and to identify and develop bioactive agents for the treatment of neuronal demyelination. The transgenic animal(s)/cell(s) of the present invention provide a model system that can be utilized to elucidate mechanisms for remyelination and for screening candidate bioactive agents. By utilizing remyelination-specific expression of markers and other means, the present invention can be utilized to assay test agents for effects on remyelination, whether the effects are positive (potentially therapeutic), or the effects are negative (potentially deleterious). Furthermore, determining the effect of the test agent upon a phenomenon associated with a remyelination may involve any suitable methods known in the art, including but not limited to those utilizing cell-based assays or techniques.

The present invention provides a recombinant nucleic acid molecule comprising a nucleic acid sequence encoding a cell death mediator protein (CDMP), wherein the nucleic acid sequence is operably linked to a neural cell-specific regulatory element. The nucleic acid sequence can also be operably linked to a second nucleic acid sequence encoding a marker protein, such as GFP or other fluorescent markers. The present invention also provides a host cell comprising a recombinant nucleic acid molecule comprising a nucleic acid sequence encoding a cell death mediator protein (CDMP), wherein the nucleic acid sequence is operably linked to a neural cell-specific regulatory element. The host cell can be a neural cell or mural cell, for example, it can be neuronal or glial cells. For example, the glial cells can be oligodendrocytes, astrocytes, microglial cells or Schwann cells. The neuronal cells can be cervical ganglion neurons, cortical neurons, serotonin neurons, dorsal root ganglion, nodose ganglion neurons, spinal motoneurons, midbrain dopaminergic neurons, central noradrenergic neurons or enteric neurons. The mural cells can be endothelial cells, pericytes or smooth muscle cells. In some embodiments, the host cell can be immune cells such as B or T lymphocytes.

Also provided is a transgenic animal comprising a nucleotide sequence encoding a cell death mediator protein (CDMP) operably linked to a cell type-specific expression regulatory element, wherein the animal exhibits a greater degree of neuropathy relative to an animal without said nucleotide sequence. The animal can be a mammal, primate, or rodent, such as a mouse, rat, guinea pig, dog, cat, rabbit, pig, chimpanzee or monkey. The neuropathy can comprise neuronal demyelination, such as multiple sclerosis. The animal can exhibits an increase in apoptotic oligodendrocytes relative to that of a control animal. The CDMP can also be ectopically confined to the central nervous system.

The nucleic acid sequence encoding the CDMP can be integrated into the genome of the host cell or animal. Alternatively, the nucleic acid sequence encoding the CDMP can be episomal. Furthermore, the recombinant nucleic acid molecule can be delivered to the host cell or animal, or to generate a transgenic animal by a viral vector, such as a lentivirus vector.

In one aspect, the CDMP can be caspase 2, caspase 5, caspase 8, caspase 9, caspase 10, or caspase 11. The CDMP can be a chimeric protein comprising a binding domain for a FK506-type ligand, a FKBP 12-type ligand, cyclosporin A-type ligand, tetracycline or steroid ligand. The expression and/or the apoptosis promoting activity of the CDMP can be inducible, for example, such as an inducible caspase 9 (iCP9). For example, the expression regulatory element can be inducible, constitutive and/or cell type or tissue-specific. In some embodiments, the expression and/or activity is specific for neural cells, such as those in an animal. The activity of the CDMP can be induced by a chemical inducer of dimerization (CID), such as AP20187.

The nucleic acid molecule comprising a nucleic acid sequence encoding a (CDMP) can be operably linked to a mural or neural cell-specific regulatory element. For example, the regulatory element can be a neuronal or glial cell specific regulatory element. The expression or activity of the CDMP encoded by the nucleic acid sequence can be specifically in neuronal or glial cells, such as in oligodendrocytes, astrocytes, microglial cells, or Schwann cells. The glial cell specific regulatory element can be from a CC1, myelin basic protein (MBP), ceramide galactosyltransferase (CGT), proteolipid protein (PLP). oligodendrocyte-myelin glycoprotein (OMG), cyclic nucleotide phosphodiesterase (CNP), NOGO, myelin protein zero (MPZ), peripheral myelin protein 22 (PMP22), protein 2 (P2), GFAP, AQP4, PDGFR-α, PDGF-α, RG5, pGlycoprotein, neurturin (NRTN), artemin (ARTN), persephin (PSPN), PDGFR-β or sulfatide gene.

In another aspect of the present invention are methods for screening biologically active, or bioactive, agents. The present invention provides a method of screening for a biologically active agent that modulates a phenomenon associated with a demyelination disorder comprising contacting a candidate agent with a cell comprising a nucleic acid encoding a cell death mediator protein (CDMP), wherein said nucleic acid is operably linked to a cell-type specific expression regulatory element; detecting an effect on the phenomenon; and, selecting the agent as effective to modulate the phenomenon if the level of activity of said CDMP is modulated relative to a control cell. The cell can be neuronal, such as a glial cell, or mural cell. The glial cell can be an oligodendrocyte, astrocyte, microglial cell, or Schwann cell.

Also provided herein is a method of screening for a biologically active agent that modulates a phenomenon associated with a demyelination disorder comprising: administering a candidate agent to a non-human transgenic animal, wherein demyelination occurs in the animal upon expression of a nucleic acid sequence encoding a cell death mediator protein (CDMP); wherein the nucleic acid sequence expression is regulated by a cell-specific expression regulatory element; activating the CDMP to effect apoptosis in at least one cell in the animal, wherein the cell is associated with a demyelination disorder; and, detecting an effect of the agent upon said phenomenon associated with said demyelination disorder. In some embodiments, the animal is allowed to recover from the demyelination prior to administration of the candidate agent. The demyelination disorder can be characterized by a loss of oligodendrocytes, astrocytes or Schwann cells in the animal and the phenomenon associated with the demyelination disorder can be characterized by a decrease in myelinated axons. In some embodiments, the demyelination disorder is multiple sclerosis. In another aspect, determining the effect of the agent can involve PCR, immunoassay, hybridization assay or a combination thereof. The candidate agent can be an antisense oligonucleotide, a peptide, an antibody, a liposome, a small interfering RNA, a small organic compound, or an inorganic compound.

In yet another aspect of the present invention, a method for compiling a profile data set for characterizing a phenomenon associated with multiple sclerosis (MS) or MS-associated condition related to multiple sclerosis comprising providing a transgenic animal or cell comprising a nucleic acid encoding a cell death mediator protein (CDMP), wherein the nucleic acid is operably linked to a neuronal- or glial-specific expression regulatory element; activating the CDMP thereby inducing apoptosis; obtaining at least one surviving neuronal or glial cell following the activation; and profiling RNA transcripts and/or encoded products in said surviving glial or neuronal cell; thereby compiling a profile data set characterizing a phenomenon associated with multiple sclerosis or MS-associated condition related to multiple sclerosis is provided.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the invention will be obtained by reference to the following detailed description that sets forth illustrative embodiments, in which the principles of the invention are utilized, and the accompanying drawings.

FIG. 1A provides a pΔcmv/mEGFP vector construct. The second generation, pΔmbpICP9/mEGFP (FIG. 1C), has a MBP specific promoter to limit gene expression to infected oligodendrocytes, and its cell specific expression causes oligodendrocyte specific cell death. The dual promoter feature allows for co-expression of GFP independent of the upstream gene so that infected cells can be easily identified using fluorescent microscopy. LTR=long terminal repeat; pCMV=cytomegalovirus promoter sequence; iCP9=engineered inducible caspase-9 gene sequence; pMND=modified LTR promoter sequence; EGFP=enhanced green fluorescent protein gene sequence; pMBP=the myelin basic protein promoter sequence.

DETAILED DESCRIPTION

Figure 1:
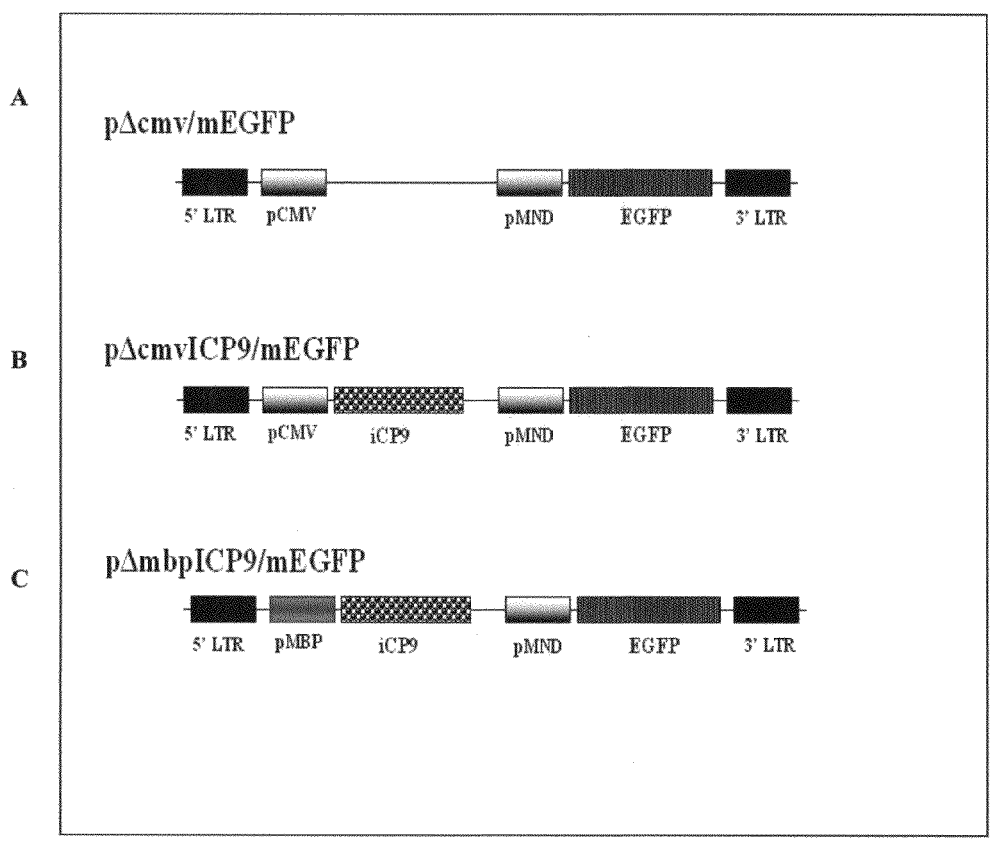
FIG. 1 illustrates engineered SIN lentiviral vectors (pΔcmvICP9/mEGFP (FIG. 1B) and pΔmbpICP9/mEGFP).

In the present invention, transgenic animals or cells provide a model system for studying neuropathy. The model system can be employed for identifying, assessing and/or quantifying neuronal health and/or demyelination/remyelination. Furthermore, compositions and methods of the invention are utilized in various embodiments for the identification and development of biologically active agents that modulate, promote or reduce neuronal or myelination health or maintenance.

One aspect of the invention encompasses selective induction of cell death in particular cell types to assess the effect on neuronal demyelination and/or remyelination. As such a neuronal response to demyelination in vivo and in vitro can be defined without artificially induced inflammation.

The loss of neurons is an important factor in the progression of disability in patients with multiple sclerosis. Furthermore, the loss of neurons may be largely independent of inflammation and may occur after the disruption of the codependent relationship between the neuron and the myelin producing oligodendrocyte cell.

Therefore in one embodiment, a system (e.g., an animal) is provided to characterize the response of neurons to the loss of its codependent oligodendrocyte cell. For example a modified retrovirus is utilized to deliver an inducible suicide gene, or a gene that encodes a cell death mediator protein, to oligodendrocytes in the brain. When the inducible factor is administered to an animal, the suicide gene induces the oligodendrocytes (myelin producing cells) to undergo apoptosis, resulting in focal demyelination that is not induced by inflammation. The response of neurons to the loss of oligodendrocytes and myelin is then characterized. By understanding the response of neurons to demyelination, interventions which protect neurons after this event can be developed.

Cells such as neural cells can be targeted in a subject or in cell culture for controlled cell death. In some embodiments, such cells are isolated from the transgenic animals of the invention for further study, for example, for assays which are conducted in a cell-based or cell culture setting, including ex vivo techniques.

Various aspects of the invention provide methods for assessing pathological changes in the CNS, such as oligodendrocyte or neuronal loss, which manifest clinically.

In some aspects of the invention, a non-human transgenic animal are engineered using methods known in the art to provide expression of a cell death mediator protein that is operably linked to a cell-type specific or inducible expression regulatory element (e.g., promoter/enhancer). In some embodiments, cells, human or non-human can be engineered to express one or more cell death mediator proteins that operably linked to a cell-type specific or inducible expression regulatory element (e.g., promoter/enhancer). Such regulatory elements useful in various aspects of the invention are described more fully herein, as well as various cell types that can be targeted with compositions/methods of the invention.

In one embodiment, expression of one or more cell death mediator protein in a non-human transgenic animal ("Test Animal") of the invention, results in a neuropathy or exacerbated neuropathy in such an animal.

In yet another embodiment, expression of one or more cell death mediator protein is in the Test Animal's central nervous system or peripheral nervous system.

In one aspect of the invention, expression of one or more cell death mediator proteins (CDMPs) results in degeneration of neurons in a Test Animal. In some embodiments, such neurons include cervical ganglion neurons, cortical neurons, serotonin neurons, dorsal root ganglion, nodose ganglion neurons, spinal motoneurons, midbrain dopaminergic neurons, central noradrenergic neurons or enteric neurons.

In various embodiments, cells that comprise cell death mediator nucleic acid constructs of the invention are, but not limited to, neural cells or mural cells.

In some embodiments, such cells are glial cells, including, but not limited to, oligodendrocytes, astrocytes, microglial cells and/or Schwann cells. In other embodiments, such cells include, but are not limited to, pericytes, endothelial cells and/or smooth muscle cells.

Another aspect of the present invention is directed to methods for determining the response of neurons and oligodendrocytes in vivo after selective and limited cell death. For example, the nucleic acid constructs of the present invention (e.g. nucleic acid constructs encoding a cell death mediator protein operably linked to a cell/tissue-specific expression regulatory element) can be applied to adult rats which result in a model system to assess the response of neurons to lesions in the CNS that is not complicated by antigen/adjuvant stimulated inflammation. Furthermore, the present invention provides compositions and methods that allow for control of lesion size, lesion location, lesion number and the temporal relationship between lesions.

General Techniques

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, $2^{nd}$ edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M.

J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Definitions

As used in the specification and claims, the singular form "a," "an," and "the" include plural references unless the context clearly dictates otherwise. For example, the term "a cell" includes a plurality of cells, including mixtures thereof.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

A "nucleotide probe" or "probe" refers to a polynucleotide used for detecting or identifying its corresponding target polynucleotide in a hybridization reaction.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR, or the enzymatic cleavage of a polynucleotide by a ribozyme.

The term "hybridized" as applied to a polynucleotide refers to the ability of the polynucleotide to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. The hybridization reaction may constitute a step in a more extensive process, such as the initiation of a PCR reaction, or the enzymatic cleavage of a polynucleotide by a ribozyme.

As used herein, "expression" refers to the process by which a polynucleotide is transcribed into mRNA and/or the process by which the transcribed mRNA (also referred to as "transcript") is subsequently being translated into peptides, polypeptides, or proteins. The transcripts and the encoded polypeptides are collectively referred to as "gene product." If the polynucleotide is derived from genomic DNA, expression may include splicing of the mRNA in a eukaryotic cell.

"Differentially expressed," as applied to nucleotide sequence or polypeptide sequence in a subject, refers to over-expression or under-expression of that sequence when compared to that detected in a control. Underexpression also encompasses absence of expression of a particular sequence as evidenced by the absence of detectable expression in a test subject when compared to a control.

The terms "polypeptide," "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

As used herein, "myelinating cell" refers to those cells capable of producing myelin which insulates axons in the nervous system. Exemplary myelinating cells are oligodendrocytes responsible for producing myelin in the central nervous system, and Schwann cells responsible for producing myelin in the peripheral nervous system.

The term "remyelinating" or "remyelination" refers to regeneration of myelin, e.g., in response to a demyelination insult.

A "subject," "individual" or "patient" is used interchangeably herein, which refers to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The "biologically active agents" or "bioactive agents" that are employed in the animal model or cell culture assays described herein may be selected from the group consisting of a biological or chemical compound such as a simple or complex organic or inorganic molecule, peptide, peptide mimetic, protein (e.g. antibody), liposome, small interfering RNA, or a polynucleotide (e.g. anti-sense). Furthermore, such agents include complex organic or inorganic molecules can include a heterogeneous mixture of compounds, such as crude or purified plant extracts.

A "promoter element" is a regulatory sequence that promotes transcription of a gene that is linked to such a sequence. The regulatory sequence can include enhancer sequences or functional portions thereof.

A "control" is an alternative subject, cell or sample used in an experiment for comparison purpose.

Cell Death Mediator Proteins (CDMPs)

The present invention provides methods and compositions comprising cell death mediator proteins (CDMPs) expressed in a cell or tissue specific manner. For example, expression may be specific to the CNS or PNS, or to specific neural or mural cells. The expression can be in an animal, and such expression in an animal can cause demyelination, for example, by inducing cell death specifically in cells with roles in myelination or remyelination. Expression can also be in vitro. The expression of the cell death mediator proteins can be inducible, in vivo or in vitro.

The cell death mediator protein has a role in mediating cell death, or apoptosis. The CDMPs may affect apoptosis directly or indirectly, for example, by modulating the activity of proteins that directly affect apoptosis. For example, the CDMP can be SMACs (second mitochondria-derived activator of caspases), IAPs (inhibitor of apoptosis proteins), caspases, or modulators of them. In other embodiments, the CDMP can be modulators of the TNF (tumor necrosis factor) receptor and other death receptor signaling pathways, such as Fas Receptor, and TRAIL receptor pathways. CDMPs can also be activators of caspases, including Granzyme B, or modulators of Granzyme B.

In various embodiments, the cell death mediator protein is encoded by a nucleic acid construct. In some embodiments, the nucleic acid construct can encode one or more CDMPs. The CDMPs can be the same or different. For example, a single nucleic can encode two of the proteins, such as two sequences encoding caspase 9 in tandem, or can encode caspase 9 and caspase 3. The nucleic acid construct of the present invention can encode caspase 2, 5, 8, 9, 10 or 11, their proenzyme forms, or derivatives thereof. In further embodiments, the sequence encoding such caspase protein(s) is modified to include a dimerization domain reactive with a cross-linker compound. Thus in some embodiments, a wild type caspase sequence is modified to produce a chimeric sequence comprising the dimerization domain selectively reactive to a cross-linker compound. Examples of such dimerization domains include those disclosed in U.S. Patent Application No. 20050187177 and U.S. Pat. No. 6,984,635, the relevant portions of which are incorporated herein by reference in their entirety.

Dimerization

In some embodiments, dimerization activates a biological process (e.g, apoptosis via activation of caspase 9), and various chimeric proteins can be utilized. The chimeric proteins are recombinant in that the various domains are heterologous to one another (derived from different sources, e.g. not found linked together in nature). Recombinant DNA constructs which comprise heterologous components, e.g, encoding a particular domain or expression control sequence, which are not found directly linked to one another in nature, are used to genetically engineer target host cells in vitro or in vivo. Cells thus engineered contain at least one such chimeric protein or a first series of genetic constructs encoding the chimeric protein(s). One such DNA construct encodes a chimeric protein comprising (a) at least one receptor domain (capable of binding to a selected ligand) fused to (b) a heterologous additional ("action") protein domain. The ligand is capable of binding to two (or more) receptor domains within the chimeric proteins, preferably with a Kd value ranging from approximately $10^{-6}$ to $<10^{-9}$ and is preferably a non-protein compound having a molecular weight less than approximately 1 kDa, 5 kDa, 10 kDa, 15 kDa or 20 kDa. The receptor domains of the chimeric proteins so oligomerized may be the same or different (i.e., homodimerization or heterodimerization). Upon exposure to the ligand and receptor oligomerization, the chimeric proteins can initiate a biological process (e.g., complement cascade). The encoded chimeric protein may further comprise an intracellular targeting domain capable of directing the chimeric protein to a desired cellular compartment, e.g., a sequence directing the protein to associate with the nucleus.

Examples of the types of ligands to which the chimeric proteins may bind include an FK506-type ligand, a cyclophilin type ligand (e.g., cyclosporin A-type ligand), tetracycline or a steroid ligand. Such binding causes oligomerization of homotypic (the same) or heterotypic (different) chimeric protein molecules. Examples of such ligands and/or receptor domains are disclosed in U.S. Pat. Nos. 5,534,418, 5,002,753, 5,298,429, 6,235,872, 6,656,971, 7,196,182, 7,101,357, 7,109,317, 7,153,685 and 7,169,564, the disclosures for each of which is incorporated by reference herein in its entirety; see also, Straathof et al., *Blood,* (2005) 105:4247-4254; Belshaw et al., *Proc Natl Acad. Sci.* (1996) 93:4604-4607.

Thus, utilizing methods described herein, target cells can comprise a DNA construct encoding a chimeric protein comprising (i) at least one receptor domain capable of binding to a selected oligomerizing ligand and (ii) another protein domain, heterologous to the receptor domain, which encodes caspase 9. Hence, following exposure to the selected ligand, oligomerization of caspase 9 expressed in such target cells can induce the apoptosis program, killing the cells comprising the DNA construct.

Caspase 9 is a protein that typically functions as a dimer after cytochrome C and ATP dependent interaction with apoptotic protease-activating factor 1 (Apaf-1). The dimerization of caspase 9 allows the polypeptide to activate downstream effectors molecules ultimately resulting in apoptosis of the cell (Springer, *J. Biochem. Mol. Biol.* (2002) 35:94-105).

Thus, in various embodiments, the cell death mediator protein is a caspase 9 chimeric protein comprising binding domains for a FK506-type ligand, cyclosporin A-type ligand, tetracycline or steroid ligand. In one embodiment, the caspase 9 comprises a FKBP12 binding domain. In further embodiments, binding domains utilized in chimeric constructs (e.g., caspase 9) may be optimized to bind a ligand (e.g., chemical inducer of dimerization).

An inducible caspase 9 cDNA (iCP9) was engineered by linking the caspase 9 cDNA sequence (GenBank AH002 818), after removal of the caspase recruitment domain (CARD), to a FK506 binding protein (FKBP) sequence (GenBank AH002818). The absence of the CARD sequence prevents physiologic dimerization of the protein and thereby prevents spontaneous initiation of the caspase cell death cascade. The fusion to the FKBP sequence allows for chemically induced aggregation after the administration of a chemical inducer of dimerization (CID). The CID, AP20187 (ARIAD Pharmaceuticals, Cambridge, Mass.) is a nontoxic synthetic FK506 analog that has been altered to prevent interaction with endogenous FKBPs. The CID system has been utilized in unrelated systems previously both in vitro and in vivo (Straathof et al., *Blood.* (2005) 105:4247-4254).

In various embodiments of the invention, nucleic acid constructs of the invention are delivered to a cell(s) (culture or in vivo) via a viral vector, including but not limited to adenovirus, adenovirus associated virus, murine leukemia virus, lentivirus, foamy virus, rabies virus or other viral vectors known in the art, such as those disclosed in U.S. Pat. No. 6,982,082.

Regulated Expression

In various aspects of the invention, cell- or tissue-specific and/or inducible expression regulatory elements are operably linked to cell death mediator proteins to effect selective cell death upon expression. As described above, tissue specific and cell specific regulatory sequences are available for expressing transgenes in the central nervous systems. The regulatory sequences allow ectopic expression of transgenes in the central nervous system or peripheral nervous system in particular cell types. For example, selective death can be achieved in cells such as, but not limited to, oligodendrocytes, microglial cells, Schwann cells or astrocytes.

Exemplary expression of regulatory sequences include regulatory sequences selected from genes including but not limited to CCl, myelin basic protein (MBP), ceramide galactosyltransferase (CGT), myelin associated glycoprotein (MAG), myelin oligodendrocyte glycoprotein (MOG), oligodendrocyte-myelin glycoprotein (OMG), cyclic nucleotide phosphodiesterase (CNP), NOGO, myelin protein zero (MPZ), peripheral myelin protein 22 (PMP22), protein 2 (P2), GFAP, AQP4, PDGFR-α, PDGF-α, RG5, pGlycoprotein, neurturin (NRTN), artemin (ARTN), persephin (PSPN), sulfatide, 2 (VEGFR2), superoxide dismutase (SOD1), tyrosine hydroxylase, neuron specific enolase, parkin gene (PARK2), parkin coregulated gene (PACRG), neuron-specific Tα1 α-tubulin (Tα1), vesicular monoamine transporter (VMAT2), and α-synuclein (SNCA), PDGFR-β or proteolipid protein (PLP).

Additional examples of neural cell-specific promoters are known in the art, such as disclosed in U.S. Patent Application Publication Nos. 2003/0110524; 2003/0199022; 2006/0052327, 2006/0193841, 2006/0040386, 2006/0034767, 2006/0030541; U.S. Pat. Nos. 6,472,520, 6,245,330, 7,022,319 and 7,033,595, the relevant disclosures of which is incorporated herein by reference; See also, the website <chinook.uoregon.edu/promoters.html>; or <tiprod.cbi.pku.edu.cn:8080/index> (listing promoters of genes specific to certain cell/tissue); and Patterson et al., *J. Biol. Chem.* (1995) 270:23111-23118.

Thus one aspect of the invention is the utilization of inducible/cell type specific expression regulatory elements for temporal control of cell death, which in turn is utilized to assess the effects of particular cells on neuronal health/maintenance or assess effects of candidate molecules on neuronal health/maintenance, as associated to neuropathies such as MS, ALS and Parkinson's.

Expression of cell death mediator proteins can also be temporally regulated by utilizing expression systems other than those utilizing cell/tissue-specific promoters (e.g., where an effector molecule is administered locally). Therefore, in some embodiments, a gene encoding a cell death mediator protein can be operably linked to a controllable promoter element, such as a tet-responsive promoter. For example, where and when desired an inducible agent (e.g., tetracycline or analog thereof) can be administered to cells or a subject to induce expression of cell death mediator protein in a cell/tissue specific manner (e.g., mere tetracycline is delivered in a localized/limited manner). Such a system can provide tight control of gene expression in eucaryotic cells, by including the "off-switch" systems, in which the presence of tetracyclin inhibits expression, or the "reversible" Tet system, in which a mutant of the *E. coli* TetR is used, such that the presence of tetracyclin induces expression. These systems are disclosed, e.g., in Gossen and Bujard (*Proc. Natl. Acad. Sci. U.S.A.* (1992) 89:5547) and in U.S. Pat. Nos. 5,464,758; 5,650,298; and 5,589,362 by Bujard et al.

Additional examples of inducible promoters include but are not limited to MMTV, heat shock 70 promoter, GAL1-GAL10 promoter, metallothien inducible promoters (e.g., copper inducible ACE1; other metal ions), hormone response elements (e.g., glucocorticoid, estrogen, progestrogen), phorbol esters (TRE elements), calcium ionophore responsive element, or uncoupling protein 3, α human folate receptor, whey acidic protein, prostate specific promoter, as well as those disclosed in U.S. Pat. No. 6,313,373; see also, online at <biobase/de/pages/products/transpor.html> (providing a database with over 15,000 different promoter sequences classified by genes/activity); and Chen et al. *Nuc. Acids. Res.* 2006, 34: Database issue, D104-107.

Yet other inducible promoters include the growth hormone promoter; promoters which would be inducible by the helper virus such as adenovirus early gene promoter inducible by adenovirus E1A protein, or the adenovirus major late promoter; herpesvirus promoter inducible by herpesvirus proteins such as VP16 or 1CP4; promoters inducible by a vaccinia or pox virus RNA polymerases; or bacteriophage promoters, such as T7, T3 and SP6, which are inducible by T7, T3, or SP6 RNA polymerases, respectively.

In other embodiments, constitutive promoters may be desirable. For example, there are many constitutive promoters suitable for use in the present invention, including the adenovirus major later promoter, the cytomegalovirus immediate early promoter, the β actin promoter, or the β globin promoter. Many others are known in the art and may be used in the present invention. In yet further embodiments, a regulatory sequence can be altered or modified to enhance expression (i.e., increase promoter strength). For example, intronic sequences comprising enhancer function can be utilized to increase promoter function. The myelin proteolipid protein (PLP) gene comprises an intronic sequence that functions as an enhancer element. This regulatory element/region ASE (antisilencer/enhancer) is situated approximately 1 kb downstream of exon 1 DNA and encompasses nearly 100 bp. See Meng et al. *J Neurosci Res.* (2005) 82:346-356.

Furthermore, where expression of the transgene in a particular subcellular location is desired, the transgene can be operably linked to the corresponding subcellular localization sequence by recombinant DNA techniques widely practiced in the art. Exemplary subcellular localization sequences include, but are not limited to, (a) a signal sequence that directs secretion of the gene product outside of the cell; (b) a membrane anchorage domain that allows attachment of the protein to the plasma membrane or other membraneous compartment of the cell; (c) a nuclear localization sequence that mediates the translocation of the encoded protein to the nucleus; (d) an endoplasmic reticulum retention sequence (e.g. KDEL sequence (SEQ ID NO:1)) that confines the encoded protein primarily to the ER; (e) proteins can be designed to be farnesylated so as to associate the protein with cell membranes; or (f) any other sequences that play a role in differential subcellular distribution of a encoded protein product.

In some embodiments, markers for distinguishing genetically modified cells can be detected. Such markers include, but are not limited to, CCl, myelin basic protein (MBP), ceramide galactosyltransferase (CGT), myelin associated glycoprotein (MAG), myelin oligodendrocyte glycoprotein (MOG), oligodendrocyte-myelin glycoprotein (OMG), cyclic nucleotide phosphodiesterase (CNP), NOGO, myelin protein zero (MPZ), peripheral myelin protein 22 (PMP22), protein 2 (P2), galactocerebroside (GalC), sulfatide, PDGFR-β PDGFR-α PDGF-α and proteolipid protein (PLP).

In various embodiments, animals in which selective cell death, such as selective apoptosis of oligodendrocytes, is induced can also be assayed for effects on demyelination/remyelination status. For example, demyelination/remyelination phenomena can be observed by immunohistochemical means or protein analysis as known in the art. For example, sections of the test animal's brain can be stained with antibodies that specifically recognize an oligodendrocyte marker. In another aspect, the expression levels of oligodendrocyte markers can be quantified by immunoblotting, hybridization means, and amplification procedures, and any other methods that are well-established in the art. e.g. Mukouyama et al. *Proc. Natl. Acad. Sci.* (2006) 103:1551-1556; Zhang et al. (2003), supra; Girard et al. *J. Neuroscience.* (2005) 25: 7924-7933; and U.S. Pat. Nos. 6,909,031; 6,891,081; 6,903,244; 6,905,823; 6,781,029; and 6,753,456, the disclosure of each of which is herein incorporated by reference.

In yet other embodiments, animals in which selective cell death occurs in cells important for maintenance of the blood brain barrier, such as in pericytes. For example, expression a caspase, such as caspase 9 or iCP9, under the control of the PDGFR-β promoter in animals can be used to assay for effects on the blood brain barrier (BBB), such as its permeability, maintenance, or integrity. For example, sections of the test animal's brain can be stained with antibodies that specifically recognize BBB markers, such as tight junction proteins. For example, markers that may be detected include occludin and claudins, such as claudin 2, claudin 5, claudin 6, claudin 7, claudin 10, claudin 12, claudin 15, and/or claudin 19. In another aspect, the expression levels of tight junction protein marker can be quantified by immunoblotting, hybridization means, and amplification procedures, and any other methods that are well-established in the art.

BBB integrity or permeability may also be assayed by using indicators such as any dye, marker, or tracer known in the art that is utilized to determine, visualize, measure, identify or quantify blood-brain barrier permeability. Non-limiting examples include, Evans Blue and sodium fluorescein. Examples of such indicators will be apparent to one of ordinary skill in the art, and include essentially any compound that is unable to traverse an intact BBB, but is capable of traversing a more permeable BBB, as well as capable of being identified, measured or quantified.

Indicators can be enzymes, tracers or markers utilized to determine BBB permeability changes, with non-limiting examples as follows:

| Enzyme | Functions observed |
|---|---|
| Dopa-decarboxylase | Convert L-Dopa to dopamine |
| Monoamine oxidase-B | Inactivates catecholamines (5-HT) |
| Pseudocholinesterase | Deacetylates heroin to morphine |
| Cytochrome P450 | O-Demethylates codeine to morphine |
| UDP-Glucuronosyltransferase | Metabolizes 1-naphthol |
| Epoxide hydrolase | Reacts with epoxides (Benzo[a]pyre 4,5-oxide) |
| Renin | Angiotensinogen to Angiotensin I |
| Dipeptidyl dipeptidase | Enkephalin metabolism |
| ACE | Enkephalin, angiotensin I, neurotensin, and bradykinin metabolism |
| Aminopeptidase A | Metabolism of angiotensin |
| Aminopeptidase M (N) | Opioid degradation (N-terminal Tyr) |
| Glutamyl aminopeptidase | Convert angiotensin II to angiotensin III |
| Enkephalinase* (neutral Endopeptidase 24.11) | Enkephalin, Endothelin, and bradyknin degradation |
| Endopeptidase* (Endopeptidase 24.15) | Dynorphin, neurotensin, bradykinin, angiotensin II, and LHRH degradation |
| ☐Glutamyltranspeptidase | Convert leukotriene C4 to leukotriene D4 |
| Alkaline phosphatase | purine and pyrimidine metabolism |

*Enzymes in choroids plexus;
ACE: angiotensin converting enzyme;
LHRH: luteinizing hormone releasing hormone Additional examples of dyes, tracers or markers include dextran, biotin, fibrinogen, albumin, blood globulin's using Coons's reaction, Texas Red conjugated dextran (70,000 da MW), Na(+)-fluorescein (MW 376) or fluorescein isothiocyanate (FITC) labelled dextran (MW 62,000 or 145,000), or FITC-labeled dextran of molecular mass 10,000 Da (FITC-dextran-10K).

Transgenic Animals

In one aspect of the invention, a transgenic animal is generated having stably integrated into the genome a transgenic nucleotide sequence encoding a neural cell-specific regulatory element operably linked to a gene encoding a protein of interest. The expression of the gene can be under the control of an inducible promoter. In some embodiments, the cell-specificity is to neural cells (e.g. glial cells, preferably astrocytes, oligodendrocytes and/or Schwann cells; or neuronal cells, such as cervical ganglion neurons, dorsal root ganglion cells, nodose ganglion neurons, spinal motor neurons, midbrain dopaminergic neurons, central noradrenergic neurons and enteric neurons).

In a preferred embodiment, the gene encoding a protein of interest encodes a cell death mediator protein. Thus, a transgenic animal of the present invention can comprise a nucleotide sequence encoding a cell death mediator protein (CDMP) operably linked to a cell type-specific expression regulatory element; wherein the animal exhibits a greater degree of neuropathy relative to an animal without the nucleotide sequence encoding the CDMP operably linked to a cell type-specific expression regulatory element. The neuropathy may be a neuronal demyelination, such as multiple sclerosis. The transgenic animal may exhibit an increase in apoptotic oligodendrocytes relative to that of a control animal, and the expression of CDMP can be ectopically confined to the central nervous system. In some embodiments the neuropathy is due to a defect in the blood brain barrier, or due to defects in both the BBB and demyelination. For example, the neuropathy may be Amyotropic Lateral Sclerosis (ALS), Multiple Sclerosis (MS), Immune Dysfunction Muscular Central Nervous System Breakdown, Muscular Dystrophy (MD), Alzheimer's disease, Pakinson's disease, Huntington's disease, Brain Ischemia, Cerebral Palsy, Corticobasal Ganglionic Degeneration, Creutzfeldt-Jakob Syndrome, Dandy-Walker Syndrome, Dementia, Vascular Encephalitis, Encephalomyelitis, Epilepsy, Essential Tremor, Kuru-Landau-Kleffner Syndrome, Lewy Body Disease, Machado-Joseph Disease, Meige syndrome, Migraine Disorders, poliomyelitis, Multiple System Atrophy, Meningitis, Drager Syndrome, Tourette Syndrome, Hallervorden-Spatz Syndrome, Hydrocephalus, Oliovopontocerebellar atrophies, Supranucleal Palsy, or Syringomyelia.

In one embodiment, the cell death mediator protein (CDMP) is caspase 2, 5, 8, 9, 10 or 11. In another embodiment, one or more of such cell death mediator proteins are expressed in a cell, such as a neural cell or mural cell. For example, the CDMP can be targeted to the neural cells of an animal, such as glial cells. The neural cell can be, but not limited to, oligodendrocytes, astrocytes, Schwann cells, or microglial cells. Targeting can also be to the mural cells of the animal, for example mural cells such as, but not limited to, pericytes, endothelial cells, or smooth muscle cells. In some embodiments, a combination of one or more target cells is selected (e.g., neural and mural, or different neural cells, or different mural cells).

In some embodiments, expression of the CDMP is inducible. For example, CDMP may be operably linked to a regulatory element with an inducible promoter. The activity of the CDMP, such as promoting apoptosis, may also be inducible. For example, a viral vector encoding a CDMP that is induced by a CID can be directly injected into the spinal cord or brain of a non-human adult animal (e.g., rat) and a CID is administered. The CID can be administered concurrent with, or subsequent to, administration of the viral vector.

The extent of focal areas of oligodendrocyte loss, resulting from focal infection, can be controlled by the amount of virus administered. The response of surviving cells to the selective loss of oligodendrocytes can be assessed using histological, molecular and electrophysiologic assays, which are apparent to one skilled in the art. The extent of lesion size (for example, as measured by oligodendrocyte death) can be correlated with axonal loss at the lesion site. Similarly, by evaluating neurons whose axons pass through the region of cell loss, it can be determined whether a demyelinating threshold exists that once surpassed results in the loss of distant neurons. Therefore, methods of the invention provide insights into the molecular response following CNS oligodendrocyte cell loss and allow identification of candidate agents to effect temporal and environmental-based approaches to neuronal protection in multiple sclerosis. In one embodiment, the viral vector is a lentiviral vector. In a further embodiment, the viral vector is an iCP9 lentivirus (further described below).

The animal models of the present invention encompass any non-human vertebrates that are amenable to procedures yielding a neuronal demyelination condition in the animal's nervous systems, including the central and peripheral nervous system. Preferred model organisms include, but are not limited to, mammals, primates, and rodents. Non-limiting examples of preferred models are rats, mice, guinea pigs, cats, dogs, rabbits, pigs, chimpanzees, and monkeys. The test animals can be wildtype or transgenic. In one embodiment, the animal is a rodent. In yet another embodiment, the animal is a mouse. In another embodiment, the animal is from a simian species. In yet another embodiment, the animal is a marmoset monkey, which is commonly utilized in examining neurological disease (e.g., Eslamboi, A. Brain Res Bull. (2005) 68:140-149; Kirik et al. Proc. Natl. Acad. Sci. (2004) 100:2884-89).

Transgenic animals can be broadly categorized into two types: "knockouts" and "knockins". A "knockout" has an alteration in the target gene via the introduction of transgenic sequences that result in a decrease of function of the target gene, preferably such that target gene expression is insignificant or undetectable, e.g. by replacing a portion of the target gene with sequences unrelated to the target gene. A "knockin" is an animal having an altered expression of a target gene, e.g., by operatively inserting a regulatory sequence of the target gene; or is an animal expressing modified copy of the target gene, e.g., by replacing the target gene with a modified copy. Modifications can be deletion or mutation of the target gene. The knock-in or knock-out animals can be heterozygous or homozygous with respect to the target genes. Both knockouts and knockins can be "bigenic," also known as double knock-in or double knock-out. Bigenic animals have at least two host cell genes being altered. In one embodiment, bigenic animal carries a transgene encoding a cell-specific cell death mediator protein and another transgenic sequence that encodes cell-specific marker genes. The transgenic animals of the present invention can broadly be classified as Knockins. In some embodiments, specific cell types of the animals may be targeted. For example, the target cells can be neural or mural. In various embodiments, neural cells include oligodendrocyte, Schwann cells, microglial cells or astrocytes, and mural cells include endothelial cells, pericytes or smooth muscle cells.

Advances in technologies for embryo micromanipulation now permit introduction of heterologous DNA into fertilized mammalian ova as well. For instance, totipotent or pluripotent stem cells can be transformed by microinjection, calcium phosphate mediated precipitation, liposome fusion, retroviral infection or other means. The transformed cells are then introduced into the embryo, and the embryo develops into a transgenic animal. In a preferred embodiment, developing embryos are infected with a viral vector containing a desired transgene so that the transgenic animals expressing the transgene can be produced from the infected embryo. In another preferred embodiment, a desired transgene is coinjected into the pronucleus or cytoplasm of the embryo, preferably at the single cell stage, and the embryo is allowed to develop into a mature transgenic animal. These and other variant methods for generating transgenic animals are well established in the art and hence are not detailed herein. See, for example, U.S. Pat. Nos. 5,175,385 and 5,175,384.

Accordingly, the present invention provides a method of using animal models for detecting and quantifying remyelination in a cell-specific manner. In such an embodiment, the method comprises the steps of: (a) inducing cell death in a cell type-specific manner by expression of cell death mediator protein in a cell; (b) allowing time for cell death to occur; (c) determining modulation of myelination/remyelination in the animal. The transgenic animals may also be used for screening bioactive agents, determining the modulation of myelination or remyelination of bioactive agents.

Animal Studies

Animal models are utilized with one or more methods of the invention to assay selective or controlled cell death in target cells related to neuropathy phenomenon (e.g. a demyelinating disorder). The phenomenon can be associated with a demyelination disorder characterized by a decrease in myelinated axon, a reduction in the levels of oligodendrocyte markers, astrocyte markers or Schwann cell markers. The demyelination disorder can be genetic, or inflicted by a pathogen or virus.

The animal models may be used to screen for bioactive agents that modulate a neuropathy. For example, the application of the model system disclosed herein, when applied to the rat CNS, provides a more accurate model that allows for the study of the neuronal response to demyelination in vivo and the development of treatments of demyelination disorders.

The present invention provides nucleic acid constructs encoding a cell death mediator protein operably linked to a cell/tissue-specific or inducible promoter that are administered to an animal to achieve expression of the cell death mediator protein and hence selective ablation of the target cells. Such expression can be achieved via ectopically maintained transgene delivery vehicles or such transgenes can be incorporated into the genome of the animal using methods known in the art. For example, expression could be achieved episomally or through stable integration of the nucleic acids encoding the CDMP.

In various embodiments, a nucleic acid construct comprising a gene encoding a cell death mediator protein ("suicide gene") is operably linked to an expression regulatory element, which is cell/tissue-specific or inducible. In various embodiments, the target cell is a neural cell or mural cell. The neural cell can be, but not limited to, oligodendrocytes, astrocytes, Schwann cells, or microglial cells. Mural cells include, but are not limited to, pericytes, endothelial cells, and smooth muscle cells. In some embodiments, a combination of one or more target cells are selected (e.g., neural and mural, or different neural cells, or different mural cells).

In yet other embodiments, the target cell is an immune cell, such as, but not limited to, B lymphocyte or T lymphocyte cell. In yet a further embodiment, B lymphocytes and/or T lymphocytes are not target cells.

In one aspect of the invention, the cell death mediator protein is a caspase protein, including but not limited to, caspase 2, 5, 8, 9, 10 or 11. In one embodiment, nucleic acid constructs of the invention comprise at least two different caspase proteins, which can be expressed in target cells. The CDMP may be chimeric, for example, CDMP with a binding domain for FK506-type ligand, cyclosporin A-type ligand, tetracycline or steroid ligand. In one embodiment, the caspase 9 comprises a FKBP12 binding domain. In further embodiments, the apoptosis promoting activity of the CDMP may be inducible, for example, binding domains utilized in chimeric constructs (e.g., caspase 9) may be optimized to bind a chemical inducer of dimerization, which promotes caspase 9 activity and thus, apoptosis.

In another aspect of the invention, methods of testing a biologically active agent for myelination/remyelination modulation activity is provided.

In one embodiment, a method for testing a candidate agent for modulation of neuropathy associated phenomenon comprises inducing cell death in a Test Animal by expression of the cell death mediator protein, allowing sufficient time for assessing effects on myelination/remyelination, administering a test bioactive agent and determining the effect on myelination/remyelination as compared to without administration, thus determining whether the test agent enhances/reduces myelination/remyelination.

Thus, in some embodiments, the method comprises the steps of: (a) inducing cell death in a cell type-specific manner; (b) assessing demyelination insult in the transgenic animal of the invention; (c) administering a test agent to the animal; (d) optionally detecting and/or quantifying expression of cell-specific marker gene(s) before and after step (c); (e) detecting if and how much remyelination has occurred in step (d); (f) determining the test agent to have remyelination modulation activity if remyelination is enhanced or diminished (e.g., by histological, histochemical, biochemical assays or by measuring expression of remyelination-specific marker proteins which can be up- or down-regulated in response to administration of the test agent). In various embodiments, detection comprises histochemical or biochemical assays known in the art. In some embodiments, detection is made at various time points and administration of the test agent can be repeated during the course of the assay, as well as using different dosing regimens.

In another embodiment, a method of testing for a compound that modulates a phenomenon associated with a neuropathy comprises administering a candidate agent to a test animal as described herein, enhancing demyelination in the test animal by inducing expression of a cell death mediator protein, determining whether administration of the candidate agent results in enhanced or reduced remyelination, thus determining that the test agent modulates a phenomenon associated with a neuropathy if remyelination is enhanced or reduced. In one embodiment, practice of the method determines whether the candidate agent modulates cell-death mediated demyelination/remyelination.

For example, in one such embodiment, a method for testing a biologically active agent that modulates a phenomenon associated with a neuropathy comprises (a) administering a candidate agent to an animal comprising a transgene encoding a death mediator protein operably linked to an inducible/cell-specific expression regulatory element; (b) inducing expression of the cell death mediator protein thus effecting cell death; and (c) determining if the candidate agent enhances myelination or remyelination. In some embodiments, detection is made at various time points and administration of a test agent can be repeated during the course of the assay, as well as using different dosing regimens. In one embodiment the neuropathy is a demyelinating disorder (e.g., MS). Levels of myelination or remyelination can be compared to control animals, and determined by methods including, but not limited to, histological, histochemical, biochemical assays or by measuring expression of remyelination-specific marker proteins which can be up- or down-regulated in response to administration of the test agent. For example, the effect of an agent upon a phenomenon associated with a demyelination disorder can involve an immunoassay, hybridization assay or PCR assay.

In various embodiments, detection comprises histochemical or biochemical assays known in the art. In some embodiments, detection is made at various time points and administration of the test agent can be repeated during the course of the assay, as well as using different dosing regimens.

The present invention also provides a method of testing a candidate agent for effects on neuron maintenance, neuron death, or neuron growth, or glial cell maintenance, glial cell death or glial cell growth.

Immunocytochemistry and histological study can be used to determine the effects on neuronal or glial maintenance, growth or death. In some embodiments, the expression of the remyelination-specific marker protein in the test animal can be compared to a control or reference animal. In other embodiments, the expression of the cell-specific marker protein in the test animal is compared to measurements made at various time points in the same animal, to determine onset or progress of neuron death or growth.

The candidate agent of the present invention may be tested by methods described herein for remyelination promoting activity, or conversely, remyelination inhibiting or reducing activity. For example, the method can comprise the steps of (a) inducing demyelination insult in the transgenic animal of the invention through expression of a cell death mediator protein in one or more particular cell types, wherein the one or more cell types affects myelination or neuronal support; (b) allowing time sufficient to effect myelin repair occur, as evidenced by expression of myelin cell-specific marker gene(s); (c) administering a candidate agent to the animal, before, during and/or after steps (a) and/or (b); (d) detecting the effect of the administered candidate on remyelination, if any.

In some embodiments, a candidate agent is administered before, during or after the inducing demyelinating insult step, for example inducing the insult by inducing the expression and/or activity of one or more CDMPs. In one embodiment, a candidate agent is administered before inducing demyelinating insult. In another embodiment, a candidate agent is administered during induction of demyelinating insult. In yet another embodiment, a candidate agent is administered after induction of demyelinating insult.

In some embodiments, a candidate agent is administered before, during or after the allowance of time sufficient to effect myelin repair. In one embodiment, a candidate agent is administered immediately after insult. In another embodiment, a candidate agent is administered during the time during which myelin repair can occur. In yet a further embodiment, a candidate agent is administered after myelin repair has occurred.

In some embodiments, a candidate agent is administered from about 1 to about 24 hours after insult. In some embodiments, a candidate agent is administered from about 1 to about 30 days after insult. In various embodiments, a candidate agent is administered from about 1, 2, 3, 4, 5, 6, 7, 8, 9, 10, 11, 12, 13, 14, 15, 16, 17, 18, 19, 20, 21, 22, 23 or 24 hours after insult. In various embodiments, a candidate agent is administered from about 1, 2, 3, 4, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days. In yet a further embodiment, a candidate agent is administered from about 1 to about 12 months.

While the amount of time required for developing remyelinated axons varies among different animals, it generally requires at least about 1 week, more often requires at least about 2 to 10 weeks, and even more often requires about 4 to about 10 weeks.

In any of the methods directed to screening a candidate agent, it should be understood that one or more candidate agents can be screened simultaneously. In various embodiments, a candidate agent is identified as enhancing remyelination, where remyelination and/or expression of myelin specific marker proteins is enhanced or increased. In some embodiments, the expression of the cell-specific marker protein in the test animal can be compared to a control or reference animal. In other embodiments, the expression of the cell-specific marker protein in the test animal is compared to measurements made at various time points in the same animal, where an earlier time point can be used as a reference or control time point. In yet other embodiments, the expression of remyelination-specific marker proteins is measure in the test animal and a control or reference animal, in determining whether a candidate agent has remyelination inhibiting or reducing activity. Such an agent can be categorized as a remyelination inhibitor or remyelination toxin.

Remeylination can be ascertained by observing an increase in the cell-specific expression of a marker gene/gene product (e.g., in the central or peripheral nervous system), such as by expression of a marker protein (e.g. EGFP). In one or more methods herein, where demyelination or myelination is sought to be identified, various markers are available in the art. Exemplary markers for identifying myelinating cells include, but are not limited to, CCl, myelin basic protein (MBP), ceramide galactosyltransferase (CGT), myelin associated glycoprotein (MAG), myelin oligodendrocyte glycoprotein (MOG), oligodendrocyte-myelin glycoprotein (OMG), cyclic nucleotide phosphodiesterase (CNP), NOGO, myelin protein zero (MPZ), peripheral myelin protein 22 (PMP22), protein 2 (P2), galactocerebroside (GalC), sulfatide, PDGFR-β PDGFR-α PDGF-α and proteolipid protein (PLP).

Subsequent to insult, such as after induction of apoptosis in myelinating cells, and after sufficient time for remyelination to occur, fluorescence of the marker proteins may be detected using in vitro or in vivo methods known in the art for detection of fluorescence in small animals. In vivo fluorescence can be detected and/or quantified utilizing devices available in the relevant art. For example, pulsed laser diodes and a time-correlated single photon counting detection system coupled to a visualization system can be used to detect the level of fluorescence emission from tissues. (Gallant et al., *Annual Conference of the Optical Society of America* (2004); Contag et al, *Mol. Microbiol.* 18:593-603 (1995; Schindehutte et al., *Stem Cells* 23:10-15 (2005)). To avoid a large signal from back-reflected photons at the tissue-air interface, the detection point is typically located at 3 mm to the right of the source point. Wavelength selection of both laser and filters is dependent on the fluorescent marker of choice. Where biological tissue absorption is low, fluorescent signals from larger tissue depths (e.g., a few to several centimeters depending on laser power) can be detected for in vivo imaging.

Mice to be imaged may be anesthetized with isoflurane/oxyten and placed on the imaging stage. Ventral and dorsal images can be collected for various time points using imaging systems available in the relevant art (e.g., IVIS imaging system, Xenogen Corp., Alameda, Calif.). Fluorescence from various target tissue can be imaged and quantified. For example, signal intensity can be presented in text or figures as a means +/− standard error about the mean. Fluorescence signals can be analyzed by analysis of variance with post hoc t tests to evaluate the difference between fluorescence signal for a given marker at time zero and each subsequent time point.

Fluorescence visualization, imaging or detection can be made using methods known in the art and described herein, supra. Visualization, imaging or detection can be made through invasive, minimally invasive or non-invasive techniques. Typically, microscopy techniques are utilized to detect or image fluorescence from cells/tissue obtained from the transgenic animals, from living cells, or through in vivo imaging techniques. Supra, "General Methodologies".

Luminescent, fluorescent or bioluminescent signals are easily detected and quantified with any one of a variety of automated and/or high-throughput instrumentation systems including fluorescence multi-well plate readers, fluorescence activated cell sorters (FACS) and automated cell-based imaging systems that provide spatial resolution of the signal. A variety of instrumentation systems have been developed to automate detection including the automated fluorescence imaging and automated microscopy systems developed by Cellomics, Amersham, TTP, Q3DM, Evotec, Universal Imaging and Zeiss. Fluorescence recovery after photobleaching (FRAP) and time lapse fluorescence microscopy have also been used to study protein mobility in living cells.

Visualizing fluorescence (e.g., marker gene encoding a fluorescent protein) can be conducted with microscopy techniques, either through examining cell/tissue samples obtained from an animal (e.g., through sectioning and imaging using a confocal microscope), examining living cells or detection of fluorescence in vivo. Visualization techniques include, but are not limited to, utilization of confocal microscopy or photo-optical scanning techniques known in the art. Generally, fluorescence labels with emission wavelengths in the near-infrared are more amenable to deep-tissue imaging because both scattering and autofluorescence, which increase background noise, are reduced as wavelengths increase. Examples of in vivo imaging are known in the art, such as disclosed by Mansfield et al., *J. Biomed. Opt.* 10:41207 (2005); Zhang et al., *Drug Met. Disp.* 31:1054-1064 (2003); Flusberg et al., *Nat. Meth.* 2:941-950 (2005); Mehta et al., *Curr Opin Neurobiol.* 14:617-628 (2004); Jung et al., *J. Neurophysiol.* 92:3121-3133 (2004); U.S. Pat. Nos. 6,977,733 and 6,839,586, each disclosure of which is herein incorporated by reference.

One example of an in vivo imaging process comprises one week before the in vivo imaging experiment, the dorsal hair in telogen is depilated (about 2.5 cm×2.5 cm area) using a depilatory agent (Nair, Carter-Wallace Inc.). On the day of the imaging experiment, the mouse is anaesthetized and placed with its dorsal skin on a microscope coverslip on the microscope stage. The depilated area of the epidermis is illuminated by a 50 W mercury lamp and scanned using an inverted laser scanning confocal fluorescent microscope (Zeiss LSM 510) with a ×10 objective and an LP 520 emission filter (Zeiss). A laser, such as Argon laser (488 nm) and a ×10 objective can image fluorescence emissions, progressively more effectively from deep tissue up to the epidermal cells. By utilizing enhanced emitters or longer wavelength emitters, the sensitivity for deeper tissue imaging can be enhanced. Alternatively small animals, such as mice can easily be scanned/imaged utilizing various different positions (e.g., dorsal, ventral, etc.). In vivo imaging has been effective even with deep tissue regions, such as liver. (e.g., Zhang et al., supra).

Cell/tissue sections mounted with Vectashield mounting medium with DAPI (Vector Laboratories) can be visualized with a Zeiss Axioplan fluorescence microscope. Images can be captured using a Photometrics PXL CCD camera connected to an Apple Macintosh computer using the Open Lab software suite. Fluorescence of different wavelengths is detected and quantified by counting positive cells within the median of the corpus callosum, confined to an area of approximately 0.04 mm$^2$. Additional methods for detecting and measuring levels of fluorescence from tissue/cell in vitro utilizing fluorescence or confocal microscopy are known in the art and can be utilized in detecting or measuring fluorescence from one or more marker proteins disclosed herein above.

In another example, neural cells can be imaged with an Axiovert S100 TV inverted microscope fitted with Ludl filter wheels (CarlZeiss, Thornwood, N.Y., USA) in the epifluorescence excitation and emission paths, and a cooled charge-coupled device (CCD) camera (Micro-MAXO; Roper Scientific, Trenton, N.J., USA) can be used to collect the images. Specific excitation and emission filters and a common dichroic element can be used to isolate the signals of the two different fluorescent proteins (HQFITC and Texas Red excitation and emission filters, and FITC/Texas Red V3 dichroic; Chroma Technology, Brattleboro, Vt., USA). The filter wheels and camera can be controlled by software (e.g., IPLabs software, Scanalytics, Fairfax, Va., USA). Sets of the red and green fluorescent images can be collected to analyze the relative percentage of cells that have red or green fluorescence. The images may be analyzed and prepared for publication with IPLabs and Adobe InDesign software. Manipulations of the images may be confined to merging the grayscale images of the red and green fluorescent proteins to create RGB color files, adjusting the brightness/contrast of the final printouts to match most closely what is observed through the microscope and adding lettering and a scale bar. Fluorescence microscopy apparatus are known in the art and commercially available. See, e.g., website at <confocal-microscopy.com/website/sc_llt.nsf.>

In an alternative embodiment, fluorescence detection is directly from the retina or cornea. The retinal site is a non-invasive locus for study of systemic toxicity. The cornea is, particularly well suited to assessing toxicity of substances applied directly to an organ containing glial cells without invading the body. Therefore, fluorescence emitted from neural cells differentially expressing a marker protein can be detected by using confocal microscopy of the retina or cornea by training the laser beam onto the desired region and detecting the level of fluorescence emitted.

Moreover, demyelination/remyelination phenomena can be observed by immunohistochemical means or protein analysis known in the art. For example, sections of the test animal's brain can be stained with antibodies that specifically recognize an oligodendrocyte marker. In another aspect, the expression levels of oligodendrocyte markers can be quantified by immunoblotting, hybridization means, and amplification procedures, and any other methods that are well-established in the art. e.g., Mukouyama et al., *Proc. Natl. Acad. Sci.* 103:1551-1556 (2006); Zhang et al., supra; Girard et al., *J. Neurosci.* 25:7924-7933 (2005); and U.S. Pat. Nos. 6,909,031; 6,891,081; 6,903,244; 6,905,823; 6,781,029; and 6,753,456, the disclosure of each of which is herein incorporated by reference.

In another aspect, cell/tissue from the central or peripheral nervous system can be excised and processed for the protein, e.g., tissue is homogenized and protein is separated on an SDS-10% polyacylamide gel and then transferred to nitrocellulose membrane to detect marker proteins. Fluorescent protein levels can be detected utilizing primary antibody/antisera (e.g., goat polyclonal raised against a particular marker protein; BD Gentest, Woburn, Mass.) and peroxidase-conjugated secondary antibody (e.g. rabbit anti-goat IgG, Sigma-Aldrich). Chemiluminescence is detected using standard reagents available in the art to detect and determine levels of fluorescence marker proteins in tissue samples.

Therefore, if a candidate therapeutic/drug or test bioactive agent is being assayed in one or more methods of the invention, then it can be determined if there is an overall difference in response to the drug compared at different time points, as well as compared to reference or controls.

Demyelination

In one aspect of the present invention, compositions and methods of the invention are utilized to effect focal demyelination, without a requirement for systemic antigen delivery, or adjuvant priming to initiate an immune response. In various embodiments of the invention, expression of cell death mediator proteins in a cell-specific manner is utilized for inducing cell death in target cells and/or neuronal loss. Expression and/or activity of the cell death mediator protein can also be inducible.

The CDMP can be SMACs (second mitochondria-derived activator of caspases), IAPs (inhibitor of apoptosis proteins), caspases, or modulators of them. In other embodiments; the CDMP can be modulators of the TNF (tumor necrosis factor) receptor and other death receptor signaling, pathways, such as Fas Receptor, and TRAIL receptor pathways. CDMPs can also be activators of caspases, including Granzyme B, or modulators of Granzyme B.

In various embodiments, the cell death mediator protein is encoded by nucleic acid constructs. In some embodiments, the nucleic acid construct can encode one or more CDMPs. The CDMPs can be the same or different. For example, a single nucleic can encode two of the proteins, such as two sequences encoding caspase 9 in tandem, or can encode caspase 9 and caspase 3. The nucleic acid construct of the present invention can encode caspase 2, 5, 8, 9, 10 or 11, their proenzyme forms, or derivatives thereof. In further embodiments, the sequence encoding such caspase protein(s) is modified to include a dimerization domain reactive with a cross-linker compound. Thus in some embodiments, a wild type caspase sequence is modified to produce a chimeric sequence comprising the dimerization domain selectively reactive to a cross-linker compound. Examples of such dimerization domains include those disclosed in U.S. Patent Application No. 20050187177 and U.S. Pat. No. 6,984,635, the relevant portions of which are incorporated herein by reference in their entirety.

Furthermore, selective cell death in vivo or in vitro can be achieved by use of a dual promoter, self-inactivating (SIN) lentiviral vector constructed to allow tissue specific expression of suicide gene or CDMP, and a marker gene (e.g., eGFP). In one embodiment, cells such as oligodendrocytes are targeted using a nucleic acid construct of the present invention, as shown in FIG. 1. The resulting vector allows for tissue specific expression of a suicide gene and the marker gene eGFP. Therefore, the vector allows for infection of post-mitotic cells such as oligodendrocytes. Furthermore, the vector can be utilized to produce high viral titers to facilitate efficient application in vivo. Thus in one embodiment, the result of such cell specific expression is oligodendrocyte specific cell death.

The dual promoter feature allows for co-expression of GFP independent of the upstream gene so that infected cells can be easily identified using fluorescent microscopy. Other fluorescent markers known in the art can be used instead of GFP.

In one embodiment, a nucleic acid delivery vehicle is utilized to deliver a sequence encoding a cell death mediator protein (or suicide protein) to cells in vitro. Delivery can also be to the CNS, in a focal pattern. There are several advantages to this system.

First, the location of the lesion can be pre-determined, allowing for accurate detection of associated neurons and cellular responses. Second, the size of the lesion produced can be controlled and altered in subsequent experiments. This is significant as there may be a threshold of oligodendrocyte loss that must be breached to propagate the death of associated neurons. Thirdly, the model allows for the ability to designate the exact timing of demyelination.

Therefore, the temporal description of neuronal response at the cellular and molecular levels can be achieved. Furthermore, the temporal relationship of one lesion to a second lesion produced at a different location in the CNS can be examined to determine if the time between demyelinating lesions is a significant factor in determining the type of CNS response. In addition, the delivery vector incorporates cell-specific expression regulatory sequent resulting in cell type-specific (e.g., oligodendrocyte specific) expression of the cell death mediator protein. This feature ensures that the experimentally imposed death of cells is limited to the desired cell type population with minimal bystander effect. Finally, the model is amenable to modification and incremental levels of complexity.

For example, in one embodiment, the iCP9 is cloned into a lentiviral plasmid and a MBP promoter sequence is cloned upstream of the iCP9 gene. The resultant lentiviral vector, pΔmbpICP9/mEGFP, is used to create replication incompetent virus (see Example 1). Thus, the vector can be utilized to define neuronal response over a period of time or at specific time points as a result of one or more particular cell types (e.g., neural and/or mural cells, as desired) by selection of cell/tissue-specific or inducible expression regulatory sequences.

In various embodiments, utilizing methods of the present invention, the response of neurons to oligodendrocyte loss can be defined over time. This can be accomplished by observing changes in known survival, trophic and apoptotic pathways as well as through microarray analysis to identify novel responses to such events. Furthermore, classification of the defined neuronal response to environmental stress includes the expression of apoptosis inducing factors, anti-apoptosis factors, neurotrophic factors and neurotrophic related transcription factors.

Therefore, in various embodiments animals/cells of the present invention can be utilized to screen various factors/compounds to determine if such factors/compounds enhance/diminish neuron maintenance or health. For example, multiple transcription factors are expressed in neurons in response to external stimuli. Two highly conserved and well defined transcription factors, NF-κB and cAMP response element binding protein (CREB), are expressed when neurons are stressed and subsequently activates, in a partially defined manner, an extensive number of downstream targets. NF-κB is modulated by physiological and pathological conditions including stroke, cardiac arrest and global ischemia, seizure and experimental exposure to glutamate, glucose deprivation and β-amyloid peptide. This highly conserved response to variable insults suggests a basic cellular response that is pertinent to neuron survival and control of apoptosis. Similarly, CREB is activated in response to a vast array of physiological stimuli. Initial in vitro studies and later in vivo studies utilizing CREB null mice suggest that CREB is necessary for survival of multiple neuronal subtypes. CREB is activated in response to hypoxia, ischemia and oxidative stress in multiple rodent models and inactivation of CREB during these stressors typically exacerbates neuronal cell death.

Both CREB and NF-κB induced cellular response appear to primarily act in a manner that ultimately supports neuron survival. Similarly, neurotrophic factors support the growth and survival of neurons. This group of molecules includes, but is not limited to: glial derived neurotrophic factor (GDNF), ciliarly neurotrophic factor (CNTF), brain derived neurotrophic factor (BNDF), nerve growth factor (NGF), NT-3 and NT 4/5. These factors are thought to be upregulated after acute CNS insult. Furthermore, oligodendrocytes are thought to provide trophic support to neurons. In vivo observations describing the loss of oligodendrocytes in acute MS lesions, in transgenic mice lacking PLP and after, irradiation of oligodendrocyte precursors at birth, have been corroborated by in vitro studies. Specifically, the addition of oligodendrocytes precursor cells or their conditioned media to the substantia nigra significantly enhanced neuronal survival. Similarly, optic nerve oligodendrocyte precursor cells or their cultured media significantly enhanced retinal ganglionic cell survival. NGF, BDNF, GDNF, Neuregulin and NT-3 have all been identified in oligodendrocyte cultured media.

In contrast to neuronal survival, programmed cell death of neurons may be an important response to acute oligodendrocyte loss. Fas, a member of the death receptor family, induces apoptosis when bound by its ligand FasL by activation of the caspase cascade. In the brain, cortical neurons express Fas and in vitro, these cells rapidly undergo apoptosis after Fas activation. In models of stroke, Fas expression is upregulated in neurons, which co-localizes with the expression of caspase 8. Furthermore, if FasL is absent, stroke-induced brain damage is reduced. In vitro cultures of motor neurons have demonstrated a similar reliance upon Fas activation for initiation of programmed cell death as motor neurons deprived of neurotrophic support in vitro were maintained in culture only after the Fas/FasL interaction was abolished.

Finally, the expression of anti-apoptotic factors may be an important aspect of the response to acute demyelination. The apoptotic process of naturally occurring cell death is highly conserved among species, and studies in the nematode *C. elegans* initially led to the identification of a molecule essential to this process and subsequently allowed for the identification of a mammalian homolog, E4BP4. This molecule has been shown to be expressed by motor neurons at the time of naturally occurring cell death in developing brain. Moreover, in vivo overexpression increases the number of neurons innervating targets suggesting that the molecule prevents the naturally occurring apoptotic process.

Therefore, in various embodiments, an anti-apoptotic compound can be administered at various time points to cells or animals of the present invention to determine anti-apoptotic compound's effects on neuron maintenance. The anti-apoptotic compound can have known activity against a cell death mediator protein (e.g., anti-caspase 9) or it can be a candidate agent that is screened to determine anti-apoptotic activity.

Thus, by defining the neuronal response over time to oligodendrocyte loss, it can be determined what compounds affect the cascade of events that ultimately leads to neuronal loss, or the rescue of neurons from cell death. The information gained from defining spatial and temporal expression patterns of molecules is critical in designing appropriate functional studies and dissecting the cellular interactions that underlie neural response to injury In one embodiment, methods of the present invention are utilized to assay oligodendrocyte-neuron interaction that is free from systemic complications in order to define the molecular response of surviving neurons (e.g., Example 2). The transection of axons and subsequent neuronal loss in acute and chronic MS lesions, as well as in NAWM (normal appearing white matter), is a relatively recently defined aspect of this disease. Evidence suggests that the continual loss of neurons accounts for the accumulation of disability in patients.

Cell-Based Screening Assays

In some aspects of the present invention cell culture is utilized in one or more methods of the invention. Target cells can be derived from a subject and transformed (e.g. genetically modified), or the transgenic animals of the invention can be the source for cell/tissue culture. In another aspect, the cells of the present invention may be cells derived from cell lines.

In various embodiments, the practice of the present invention may involve cell-based assays for providing a comparison of the expression of a gene or gene product or the activity of the gene product in a test cell (e.g., transgenic oligodendrocyte or Schwann cell) relative to a control cell. The test cell used for this invention can be isolated from central or peripheral nervous systems, and includes cell culture derived therefrom and the progeny thereof, and section or smear prepared from the source, or any other samples of the brain that contain, for example, oligodendrocytes or Schwann cells or their progenitors. Where desired, one may choose to use enriched cell cultures that are substantially free of other neuronal cell types such as, but not limited to, neurons, glial cells, microglial cells, and astrocytes. Various methods of isolating, generating or maintaining matured oligodendrocytes and Schwann cells are known in the art and are exemplified herein.

In one embodiment, a method is provided for compiling a profile data set for characterizing a phenomenon associated with MS or MS-associated condition comprising providing a non-human transgenic animal or cell comprising a transgene encoding a cell death mediator protein, wherein the transgene is operably linked to a neuronal- or glial-specific expression regulatory element; activating the cell death mediator protein, thereby inducing apoptosis; obtaining at least one surviving neuronal or glial cell following the activation; and profiling RNA transcripts and/or encoded products in the surviving glial or neuronal cell; thereby compiling a profile data set characterizing a phenomenon associated with MS or MS-associated condition. In other embodiments, this method provides for compiling a profile data set for characterizing phenomenon associated with ALS or Parkinson's disease.

In some embodiments, the cell death mediator protein is caspase-9 or caspase-11. In one embodiment, activating caspase-9 comprises inducing dimerization of caspase-9. In another embodiment, activating caspase-11 comprises autoactivation.

In various embodiments, the cell type-specific expression regulatory element is from a gene selected from a group including one or more of CCl, myelin basic protein (MBP), ceramide galactosyltransferase (CGT), myelin associated glycoprotein (MAG), myelin oligodendrocyte glycoprotein (MOG), oligodendrocyte-myelin glycoprotein (OMGP), cyclic nucleotide phosphodiesterase (CNP), NOGO, myelin protein zero (MPZ), peripheral myelin protein 22 (PMP22), protein 2 (P2), GFAP, AQP4, PDGFα, RG5, pGlycoprotein, neurturin (NRTN), artemin (ARTN), persephin (PSPN), sulfatide, 2 (VEGFR2), superoxide dismutase (SOD1), tyrosine hydroxylase, neuron specific enolase, parkin gene (PARK2), parkin coregulated gene (PACRG), neuron-specific Tα1 α-tubulin (Tα1), vesicular monoamine transporter (VMAT2), α-synuclein (SNCA), PDGFR-α, PDGFR-β, or proteolipid protein (PLP).

In one embodiment, the present invention provides a method of identifying a candidate biologically active agent that modulates remyelination. The method involves the steps of obtaining or isolating transgenic cells from transgenic animals of the present invention that are capable of cell-differential expression of cell death mediator protein, culturing such cells; contacting a candidate agent with the cultured cells; detecting an altered expression of a gene or gene product or an altered activity of the gene product relative to a control cell, the gene or gene product being correlated to modulation of cell death by the cell death mediator protein; and selecting the agent as a candidate if the level of expression of said gene or gene product is modulated relative to said control cell.

In another embodiment, an agent is determined to be a candidate agent if the number of target cells undergoing cell death is modulated by addition of the candidate agent as compared to control cells.

In another embodiment, the present invention provides a method of identifying a biologically active agent that promotes remyelination. The method comprises the steps of obtaining, isolating and culturing target cells from a demyelinated lesion present in a transgenic animal of the present invention; contacting a candidate biologically active agent with the cultured cells; and detecting an altered expression or an altered activity of a transgene encoding a cell death mediator protein; and selecting the agent as a candidate if the level of expression of the gene or gene product, or the level of activity of the gene product is increased relative to the control cell. For example, if a candidate agent enhances cell death mediating activity of the cell death mediator protein, then the candidate can promote demyelination, whereas if said candidate agent reduces cell death mediating activity then the agent can promote remyelination.

In certain embodiments, it may be preferable to employ myelinating cells from young subjects whose nervous systems are actively undergoing myelination. In other embodiments, it may be preferable to use remyelinating cells derived from adult oligodendrocyte precursors in demyelinated lesions, including but not limited to, lesions inflicted by pathogens or physical injuries, and lesions caused by toxic agents such as cuprizone.

In one embodiment, high density cortical cultures are transfected with replication-deficient lentivirus expressing iCP9. After addition of a CID (chemical inducer of dimerization) and subsequent death of oligodendrocytes, microarray analysis of gene transcription can be used to assess the expression of novel factors in surviving cultured cells. The extent of oligodendrocyte cell death in these cultures will be systemically varied to identify molecular responses related to the severity of cell destruction. Therefore, in various embodiments, one or more molecular targets modulating cell death are identified.

Various genetic vehicles suitable for the present invention are available in the art. They include both viral and non-viral expression vectors. Non-limiting exemplary viral expression vectors are vectors derived from RNA viruses such as retroviruses, and DNA viruses such as adenoviruses, foamy virus, rabies virus and adeno-associated viruses. Non-viral expression vectors include but are not limited to plasmids, cosmids, and DNA/liposome complexes. The genetic vehicles can be engineered to carry regulatory sequences that direct tissue specific, cell specific, or even organelle specific expression of the exogenous genes carried therein.

In some embodiments, target cells can be co-transfected with multiple genetic vehicles (e.g., two vectors each of which comprises gene constructs encoding a desired product and gene constructs encoding one or more reporter genes).

Furthermore, if desired a wide variety of subcellular localization sequences or signals have been characterized and are applicable for directing organelle specific expression of transgenes. For instance, subcellular localization sequence can be any one of the following: (a) a signal sequence that directs secretion of the gene product outside of the cell; (b) a membrane anchorage domain that allows attachment of the protein to the plasma membrane or other membraneous compartment of the cell; (c) a nuclear localization sequence that mediates the translocation of the encoded protein to the nucleus; (d) an endoplasmic reticulum retention sequence (e.g. KDEL sequence (SEQ ID NO: 1)) that confines the encoded protein primarily to the ER; (e) a protein of interest can be farnesylated, such that the protein will be membrane associated; or (f) any other sequences that play a role in differential subcellular distribution of a encoded protein product.

If desired, the genetic vehicles can be inserted into a host cell (e.g., myelinating cells such as oligodendrocytes or Schwann cells) by any methods known in the art. Suitable methods may include transfection using calcium phosphate precipitation, DEAE-dextran, electroporation, or microinjection.

The selection of an appropriate control cell or tissue is dependent on the test cell or tissue initially selected and its phenotypic or genotypic characteristic which is under investigation. Whereas the test remyelinating cell is contacted with a test compound, then a control cell or tissue may be a non-treated counterpart. Whereas the test remyelinating cell is a test cell detected post demyelination, the control cell may be a non-treated counterpart. It is generally preferable to analyze the test cell and the control in parallel.

As discussed in the sections above, these cells are useful for conducting cell-based assays for elucidating the molecular bases of neuronal remyelination conditions, and for assaying agents effective for inhibiting neuronal demyelination or promoting remyelination.

In some aspects of the invention, transgenic cells can be obtained from the transgenic animals of the invention, cultured and expanded, transduced with a gene encoding a target protein, and implanted or reintroduced into the source animal or some other animal. In such ex vivo methods, the transgenic cells can be transfected with a gene encoding a biologically active agent (e.g., gene encoding a test product) that can be inducibly produced for example, so as to assay the test gene/protein for modulation of marker gene expression/production. Such modulation can be assayed in cell-culture as described herein above. Alternatively, transduced cells are reintroduced into the subject animal, where marker gene expression can be assayed and compared to a control or reference, where the cells transplanted are not transduced, do not express a vector-borne product of interest, express a vector-borne product of interest in a time controlled manner (e.g., inducible expression) or express the product of interest constitutively (e.g., CMV promoter).

For example, glial cells (e.g., oligodendrocytes or Schwann cells) can be derived from nerve biopsies. Cells can be expanded in culture (e.g., utilizing proliferating medium composed of DMEM containing 10% heat-inactivated fetal bovine serum (FBS) and supplemented with antibiotics, recombinant Neu differentiation factor (NDF), insulin and forskolin (1 μg/ml). Furthermore, cells can be sorted from non-transgenic nerve cells utilizing the fluorescence labels provided by the transgene(s) (e.g., FACS). For transduction, cells can be transfected with various vector vehicles known in the art that will deliver a product of interest. Therefore, in various embodiments, the nucleic acid constructs of the invention are also operably linked to one or more sequences encoding a marker protein.

Vectors that can be utilized with one or more composition or methods of the present invention include derivatives of SV-40, foamy virus, rabies virus, adenovirus, lentivirus, retrovirus-derived DNA sequences and shuttle vectors derived from combinations of functional mammalian vectors and functional plasmids and phage DNA. Eukaryotic expression vectors are well known, e.g. such as those described by P J Southern and P Berg, *J Mol Appl Genet.* 1:327-341 (1982); Subramini et al., *Mol. Cell. Biol.* 1:854-864 (1981), Kaufmann and Sharp, *J Mol. Biol.* 159:601-621 (1982); Scahill et al., *PNAS USA* 80:4654-4659 (1983) and Urlaub and Chasin *PNAS USA* 77:4216-4220 (1980), which are hereby incorporated by reference. The vector used in the methods of the present invention may be a viral vector, such as a retroviral vector, such as replication deficient adenoviruses. For example, a "single gene vector" in which the structural genes of a retrovirus are replaced by a single gene of interest, under the control of the viral regulatory sequences contained in the long terminal repeat, may be used, e.g., Moloney murine leukemia virus (MoMulV), the Harvey murine sarcoma virus (HaMuSV), murine mammary tumor virus (MuMTV) and the murine myeloproliferative sarcoma virus (MuMPSV), and avian retroviruses such as reticuloendotheliosis virus (Rev) and Rous Sarcoma Virus (RSV), as described by Eglitis and Andersen, *BioTechniques* 6(7): 608-614 (1988), which is hereby incorporated by reference. Preferably, the vector of the present invention is a lentivirus vector.

In one embodiment, an engineered inducible caspase 9 (iCP9) cDNA sequence is cloned into a lentiviral vector under the control of the myelin basic protein gene promoter sequence FIG. 1C. Subsequently, replication incompetent lentivirus can be produced from this plasmid and applied to cellular and animal systems. Although the virus will result in infection of all cell types exposed, expression of the iCP9 gene will be limited to oligodendrocytes because of the cell specific promoter system. The addition of a chemical inducer of dimerization (CID) will result in the cellular death of only oligodendrocytes. This approach will be highly effective at specifically killing oligodendrocytes both in vitro and in vivo. One of skill in the art recognizes that other CDMPs may be substituted for iCP9, such as other caspases or their derivatives, that other promoter sequences may be substituted for the MBP promoter. In another aspect of the present invention, microarray or other expression profiling processes known in the art are utilized to identify a gene or sets of genes that are upregulated or downregulated in response to cell death. In various embodiments, the expression data sets can be compiled for various and particular time points, including before, during and after induction of cell death (e.g., Example 5).

Bioactive Agent

A biologically active agent or bioactive agent effective to modulate neuronal remyelination is intended to include, but not be limited to, a biological or chemical compound such as a simple or complex organic or inorganic molecule, peptide, peptide mimetic, protein (e.g. antibody), liposome, small interfering RNA, or a polynucleotide (e.g. anti-sense).

A vast array of compounds can be synthesized, for example polymers, such as polypeptides and polynucleotides, and synthetic organic compounds based on various core structures, and these are also contemplated herein. In addition, various natural sources can provide compounds for screening, such as plant or animal extracts, and the like. It should be understood, although not always explicitly stated, that the active agent can be used alone or in combination with another modulator, having the same or different biological activity as the agents identified by the subject screening method.

When the biologically active agent is a composition other than naked RNA, the agent may be directly added to the cell culture or added to culture medium for addition. As is apparent to those skilled in the art, an "effective" amount must be added which can be empirically determined. When the agent is a polynucleotide, it may be introduced directly into a cell by transfection or electroporation. Alternatively, it may be inserted into the cell using a gene delivery vehicle or other methods as described above.

A wide variety of labels suitable for detecting protein levels are known in the art. Non-limiting examples include radioisotopes, enzymes, colloidal metals, fluorescent compounds, bioluminescent compounds, and chemiluminescent compounds.

Candidate biologically active agents identified by the subject methods can be broadly categorized into the following two classes. The first class encompasses agents that when administered into a cell or a subject, reduce the level of expression or activity of a cell death mediator protein(s). The second class includes agents that augment the level of expression or activity of a cell death mediator protein(s).

Pharmaceutical Compositions

The methods of the present invention can be utilized to select a biologically active agent that can subsequently be implemented in treatment of demyelination disorders. The selected biologically active agents effective to modulate remyelination may be used for the preparation of medicaments for treating demyelinating disorders. In one aspect, an identified/selected biologically active agent of this invention can be administered to treat neuronal demyelination inflicted by pathogens such as bacteria and viruses. In another aspect, the selected agent can be used to treat neuronal demyelination caused by toxic substances or accumulation of toxic metabolites in the body as in, e.g., central pontine myelinolysis and vitamin deficiencies. In yet another aspect, the agent can be used to treat demyelination caused by physical injury, such as spinal cord injury. In still yet another aspect, the agent can be administered to treat demyelination manifested in disorders having genetic attributes, genetic disorders including but not limited to leukodystrophies, adrenoleukodystrophy, degenerative multi-system atrophy, Binswanger encephalopathy, tumors in the central nervous system, and multiple sclerosis.

Various delivery systems are known and can be used to administer a biologically active agent of the invention, e.g., encapsulation in liposomes, microparticles, microcapsules, expression by recombinant cells, receptor-mediated endocytosis (see, e.g., Wu and Wu, (1987), *J. Biol. Chem.* 262:4429-4432), construction of a therapeutic nucleic acid as part of a retroviral or other vector, etc. Methods of delivery include but are not limited to intra-arterial, intra-muscular, intravenous, intranasal, and oral routes. In a specific embodiment, it may be desirable to administer the pharmaceutical compositions of the invention locally to the area in need of treatment; this may be achieved by, for example, and not by way of limitation, local infusion during surgery, by injection, or by means of a catheter. In certain embodiment, the agents are delivered to a subject's nerve systems, preferably the central nervous system. In another embodiment, the agents are administered to neural tissues undergoing remyelination.

Administration of the selected agent can be effected in one dose, continuously or intermittently throughout the course of treatment. Methods of determining the most effective means and dosage of administration are well known to those of skill in the art and will vary with the composition used for therapy, the purpose of the therapy, the target cell being treated, and the subject being treated. Single or multiple administrations can be carried out with the dose level and pattern being selected by the treating physician.

The preparation of pharmaceutical compositions of this invention is conducted in accordance with generally accepted procedures for the preparation of pharmaceutical preparations. See, for example, *Remington's Pharmaceutical Sciences* 18th Edition (1990), E. W. Martin ed., Mack Publishing Co., PA. Depending on the intended use and mode of administration, it may be desirable to process the active ingredient further in the preparation of pharmaceutical compositions. Appropriate processing may include mixing with appropriate non-toxic and non-interfering components, sterilizing, dividing into dose units, and enclosing in a delivery device.

Pharmaceutical compositions for oral, intranasal, or topical administration can be supplied in solid, semi-solid or liquid forms, including tablets, capsules, powders, liquids, and suspensions. Compositions for injection can be supplied as liquid solutions or suspensions, as emulsions, or as solid forms suitable for dissolution or suspension in liquid prior to injection. For administration via the respiratory tract, a preferred composition is one that provides a solid, powder, or aerosol when used with an appropriate aerosolizer device.

Liquid pharmaceutically acceptable compositions can, for example, be prepared by dissolving or dispersing a polypeptide embodied herein in a liquid excipient, such as water, saline, aqueous dextrose, glycerol, or ethanol. The composition can also contain other medicinal agents, pharmaceutical agents, adjuvants, carriers, and auxiliary substances such as wetting or emulsifying agents, and pH buffering agents.

EXAMPLES

Example 1

Production of iCP9 Virus

To Produce Replication Incompetent Virus.

Figure 2:
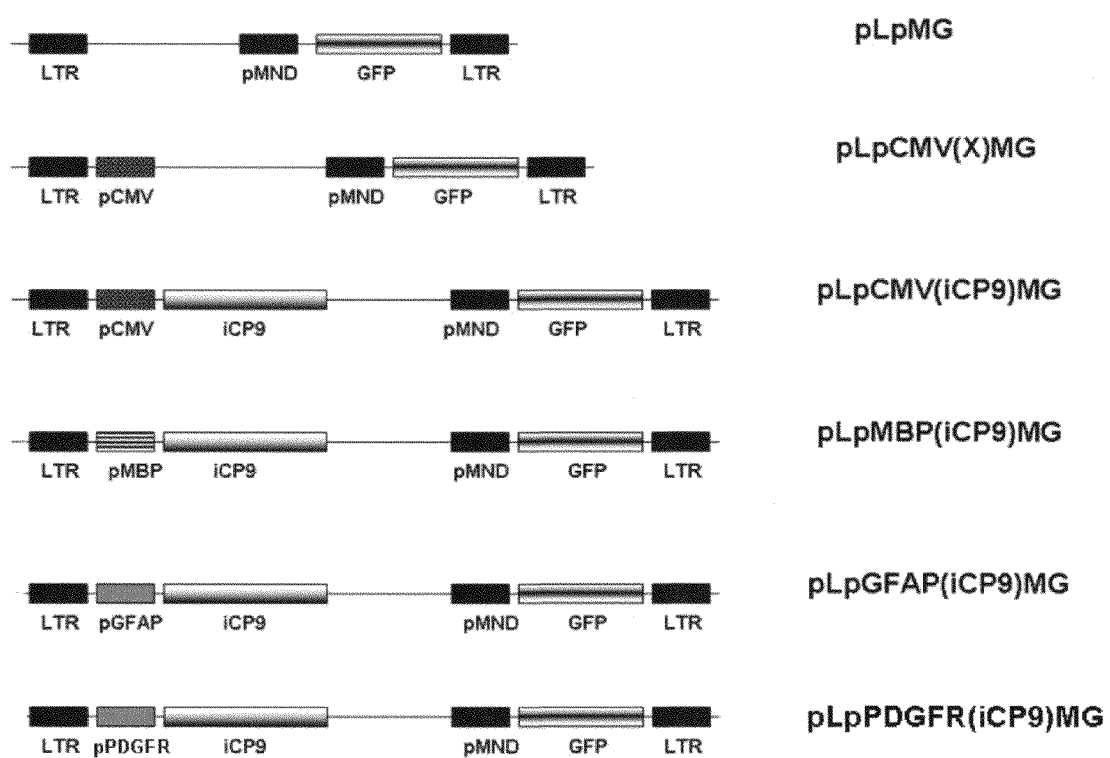
FIG. 2 illustrates lentiviral vectors created with various different tissue specific promoters to induce apoptosis in a cell-type selective manner. The viral vectors typically result in EGFP expression in infected cells. LTR=long terminal repeat; pMND=viral promoter sequence; GFP=green fluorescent protein; pCMV=cytomegalovirus promoter sequence; iCP9=inducible caspase gene sequence.
Figure 3:
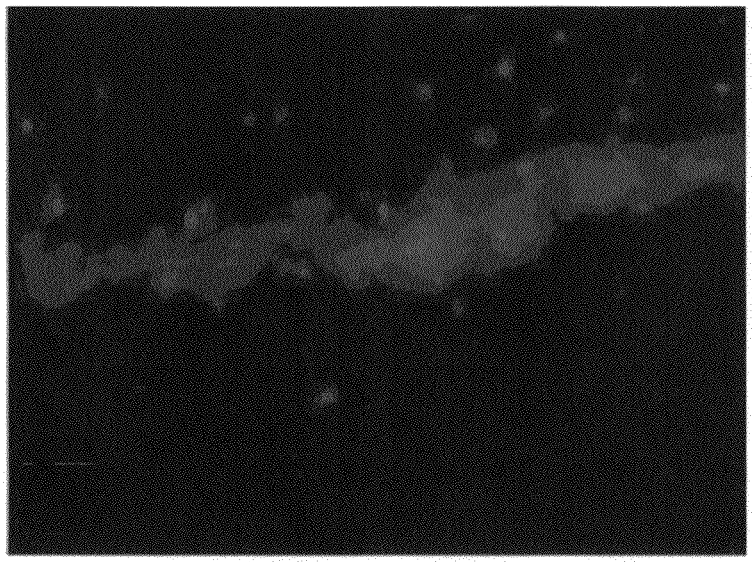
FIG. 3 provides a photograph demonstrating that concentrated lentivirus can be applied directly to the CNS and the extent and area of infection can be determined based on the number of GFP positive cells detected after sacrifice and thin section of the brain or spinal cord. This data establishes the transfer mechanism for specific cell death in vitro and in vivo
Figure 4:
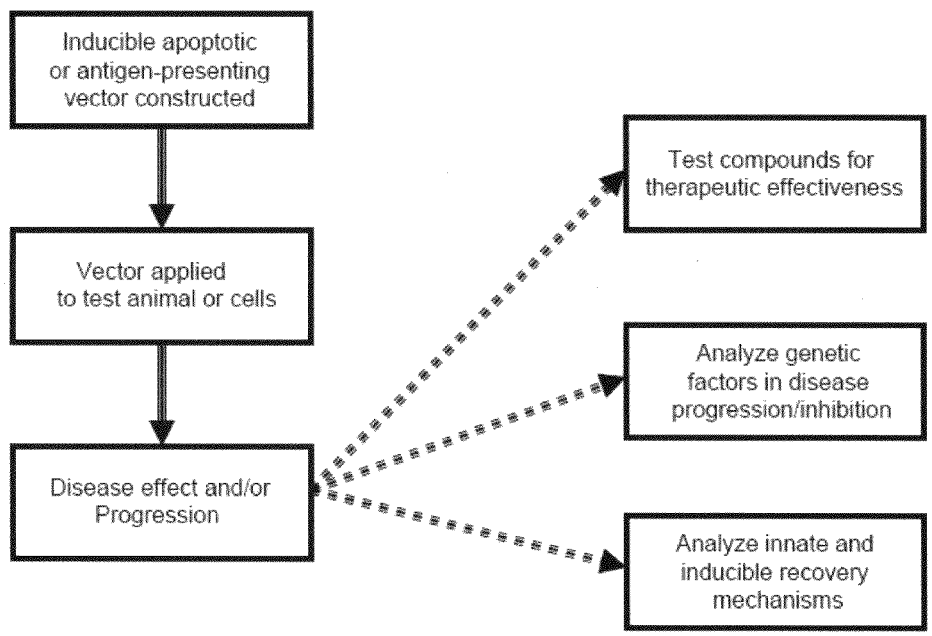
FIG. 4 is a graphical representation of certain embodiments of the present invention. The figure demonstrates a general outline of one method of the invention and certain applications for the method.

FIGS. 1 and 2 depicts the general schematic for the transfer vectors used herein. The first generation self inactivating lentiviral vector pLpMG was modified by insertion of either the cytomegalovirus promoter sequence (pCMV), a fragment of the rat Myelin Basic Protein promoter (pMBP), a fragment of the rat glial fibriallary acid protein promoter (pGFAP) or a fragment of the platelet derived growth factor receptor (PDGFR)-alpha promoter (pPDGFR). The resulting vectors (pLpCMVXMG, pLpMBPXMG, pLpGFAPXMG, pLpPDGFRXMG) were further modified by ligation of the iCP9 cDNA sequence, obtained via PCR using the original vector (kind gift of Dr David Spencer, Baylor Medical Center) as template, was cloned downstream of the new promoter sequence.

The three vectors, pLpCMV(iCP9)MG, pLpMBP(iCP9)MG, pLpGFAP(iCP9)MG, pLpPDGFR(iCP9)MG, were then used to generate high titer, replication incompetent lentivirus. Viral titer was determined against 293T cells followed by FACS analysis for EGFP expression as all vectors co-express EGFP. All titers used in vivo were at least $10^9$ colony forming units per ml. This resulted in a vehicle to transfer the expression of the inducible suicide gene (iCP9) to cells both in vitro and in vivo while enabling identification of infected cells through EGFP expression as it will be driven off a viral promoter sequence within the same vector. It also limited the gene expression to specific cell types based on which promoter was used, which gives the system cell type specific ablation in a time controlled manner.

T cells were transfected with the pΔmbpICP9/mEGFP vector along with plasmids encoding the gag-pol and RD114 envelope protein using lipofectamine (Invitrogen, Carlsbad, Calif.). Forty-eight hours after transfection viral supernatant were harvested and either directly applied to target cells or snap frozen and stored at −80° C.

To induce timely cell death. Collected virus was used to transduce primary oligodendrocyte cultures that have been established. Cells were cultured and evaluated using fluorescent microscopy for the expression of GFP. The extent of GFP positive cells correlated with the viral infection efficacy. Cell protein isolation was conducted and protein isolates were subjected to Western blot transfer to detect stable expression of the iCP9 protein. The resultant membrane was probed with anti-caspase 9 antibody (R&D Systems Inc. #AF8301). Once the stable expression of iCP9 was confirmed at the protein level with Western blot techniques, the CID was applied to these cells in culture at a 10 nM concentration. This induced the cellular death of infected cells. Cell death was detected by viewing cultures under the fluorescent microscope and by using Methylene Blue (Sigma) viability staining of cells in culture after exposure to the CID. All experiments were run in parallel using the astrocyte-derived U87 cell line as a negative control.

Figure 5:
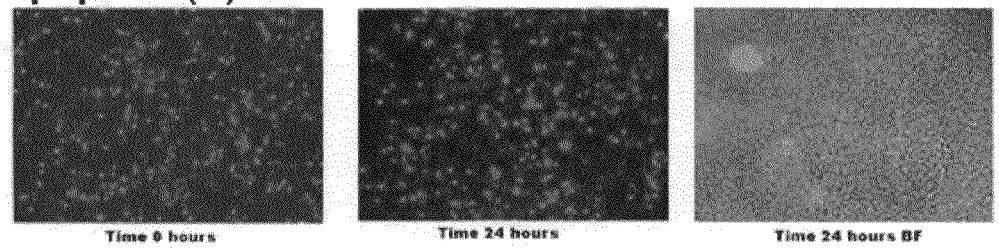
FIG. 5 provides a photograph demonstrating cells infected with control virus (top) remained viable after CID was added to culture as demonstrated by persistence of GFP+ cells. Cells infected with virus expressing iCP9 underwent apoptosis after CID exposure (bottom) as demonstrated by the absence of GFP+ cells. The persistence of cells in bright field demonstrates the specificity of apoptosis to infected cells only. BF=Bright Field.
Figure 5:
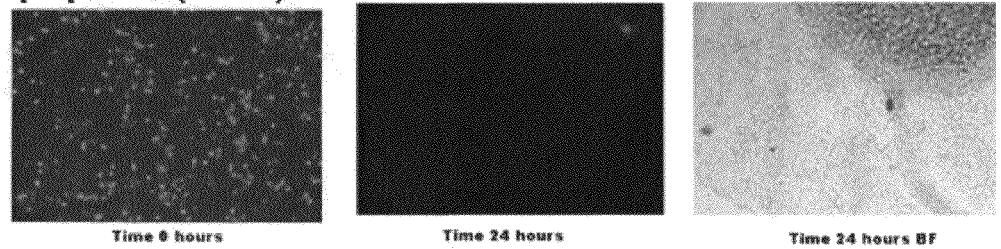
Figure 6:
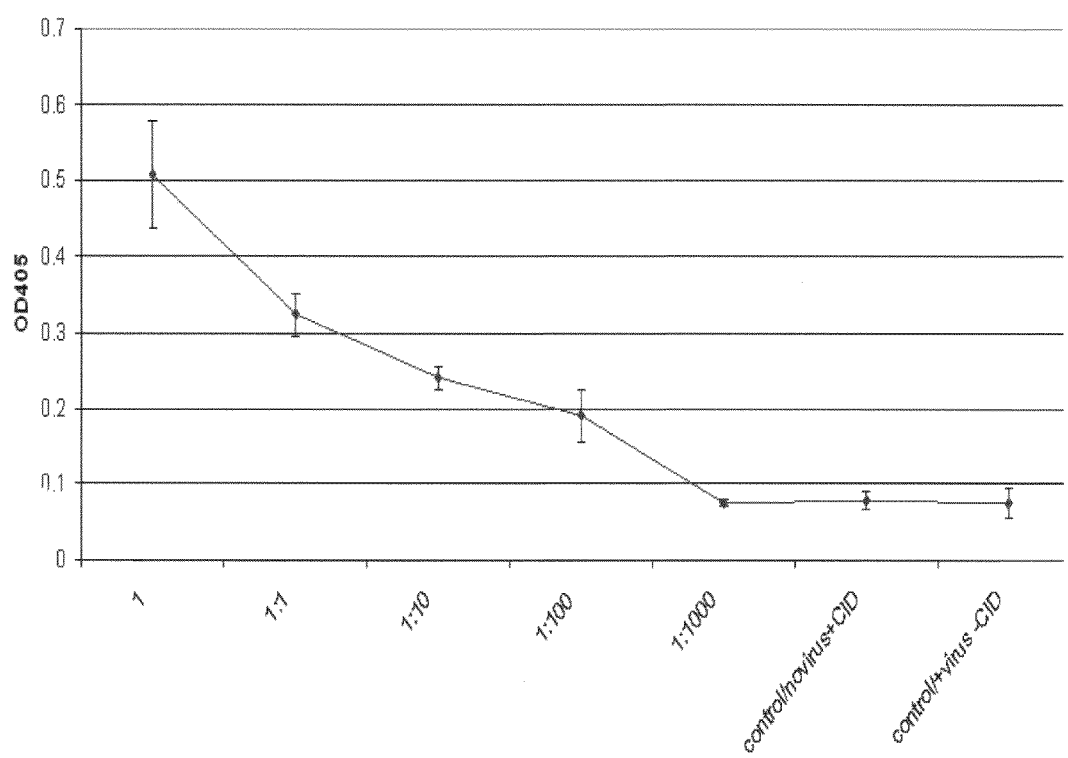
FIG. 6 is a graph showing cells exposed to various dilutions of virus encoding the iCP9 gene and then CID was added to the culture media. 4 hours later, Apoptosis ELISA was performed. Apoptosis levels decreased with dilution of virus as fewer cells were infected and expressed iCP9. Thus apoptosis correlated with iCP9 gene expression. X-axis is virus dilution. Y-axis is ELISA absorption at 405 nm.

To induce apoptosis in the presence of the CID and demonstrate the cell type selectivity, lentivirus was applied to in vitro cultures. Apoptosis was initially induced in 293T cells using the pLpCMV(iCP9)MG virus which produces constitutive expression of iCP9. EGFP is also produced from the same viral plasmid and promoter. After the addition of CID, EGFP-positive cells (corresponding to cells transfected with virus) rapidly underwent apoptosis and were not identified in culture. However, cells not transfected with virus (EGFP negative) persisted in culture. In identical cultures transfected with control virus, pLpCMVXMG, EGFP-positive cells persisted after exposure to CID (FIG. 5). A Cell Death Detection ELISA Plus (Roche Inc) was also performed to determine the level of apoptosis in culture after cells infected with various dilutions of virus were exposed to CID. The ELISA system detects histone-complexed DNA fragments that are produced by cells undergoing apoptosis. The ELISA data shows a correlation between infection, subsequent gene expression and cell death (FIG. 6).

Possible alternative cell death mediator systems include the use of an *E coli*-derived cytosine deaminase gene, the HSV-tk system and a transgenic CD20, which can be activated by a monoclonal chimeric anti-CD20 antibody to induce apoptosis.

Results demonstrated efficient infection of target cells (e.g., primary oligodendrocytes) with the pΔcmvICP9/mEGFP derived lentivirus. The infection rate should approach approximately 100% of target cells in culture based on preliminary data. Furthermore, using an MBP promoter sequence to drive oligodendrocyte specific expression of genes, GFP is detected in the oligodendrocytes and not in the U87 control cell line (or other control cell lines, e.g., NIH 3T3). Using iCP9 systems with CIDs, the administration of the CID to cultures is expected to yield rapid and efficient cell death in the oligodendrocytoma cell line, but not in the U87 cell line.

Addition of CID to in vitro system. The CID was added to the mixed cortical culture described above at a final concentration of 10 nm in Neurobasal medium with 50 ng/ml NGF. The initial time to oligodendrocyte death was thus established as described above and represents the first time point for the analysis of neuronal response. The second time point represented the subacute response at 24 and 72-hour analysis. Finally, a chronic response to oligodendrocyte loss was analyzed at 1 week, 2 weeks and 2 months post-CID administration.

Example 2

Oligodendrocyte Loss

The iCP9 cell death system was applied to oligodendrocyte primary cell cultures and the efficacy of cell death, as well as the time course, was defined. Second, the system was applied to high-density cortical cultures to model the acute loss of oligodendrocytes that occurs in MS.

Using this system the response of neurons to oligodendrocyte loss was defined over time. This was accomplished by observing changes in known survival, trophic and apoptotic pathways as well as through microarray analysis to identify novel responses to such events.

Establish primary oligodendrocyte cultures. Enriched populations of oligodendrocytes were isolated from Fischer P2 rats. Forebrain was dissected in Hank's buffered salt solution. Tissue will be cut into approximately 1-mm pieces in a poly L-lysine-coated 25 cm$^2$ flask, and then incubated at 37° C. for 15 minutes in a humidified 5% $CO_2$ room air incubator in 0.01% trypsin and 10 μg/ml DNase. Following this incubation period, DMEM medium supplemented with 20% fetal calf serum (FCS) was added to the tissue mixture and then left to proliferate for 10 days in a humidified 5% $CO_2$ room air incubator. After ten days oligodendrocyte precursor cells (A2B5$^+$) was collected by shaking the flask over-night at 200 rpm at 37° C. The cells that remain adherent to the flask were cultured in high-glucose DMEM supplemented with fibroblast growth factor (FGF) and platelet derived growth factor (PDGF) to a final concentration of 10 ng/ml for one week. Afterwards, FGF and PDGF were removed from the culture medium allowing for A2B5+ cells to differentiate into O4+ premyelinating oligodendrocytes over 3 to 7 days and then to O4+ and MBP+ mature oligodendrocytes after 7-10 days. The status of cellular differentiation was monitored by noting the change in cellular morphology in culture. Differentiation into mature, MBP+ oligodendrocytes can be easily identified with microscopic examination. To confirm the differentiation, the pattern was observed with light microscopy as changes in cell morphology, anti-A2B5, anti-O4 and anti-MBP antibodies were utilized in basic immunohistochemical staining protocols using an aliquot of cultured cells at various time points in the differentiation pathway.

Once this system and differentiation pattern was confirmed, A2B5$^+$ primary cell cultures were cultured in pΔmbpICP9/mEGFP viral supernatant for 8 hours. After eight hours supernatant was removed and replaced with DMEM/FGF PDGF medium for 24 hours. Cells were then be visualized under fluorescent microscopy to determine the efficacy of infection. Infected cells expressed EGFP and were readily identified using the proper fluorescent filter system.

After efficient infection with pΔmbpICP9/mEGFP is confirmed, aliquots of cultured GFP$^+$, A2B5$^+$ cells are allowed to differentiate in culture as described above. After mature, MBP$^+$ oligodendrocytes were identified in culture, the CID is added to a final concentration of 10 nM in DMEM/20% FCS. Maintaining multiple cultures allowed for the analysis of apoptosis at various time points after addition of the CID. Methylene Blue staining of cultures was undertaken at 1, 4, 12 and 24 hours after the CID is added to culture supernatant. Methylene blue positive cells are thus identifiable and represent viable cells. This experiment was run in duplicate using A2B5$^+$ cells that have not been exposed to pΔmbpICP9/mEGFP viral supernatant, and therefore, should not undergo apoptosis. Therefore, time to death for 100% of cells was established after addition of the CID.

Example 3

High Density Mixed Cortical Cultures

High density mixed cortical cultures were established after isolation of cerebral cortices from 3 Fischer rats as previously described. Cerebral cortices were removed and place in ice-cold Hanks' balanced salt solution, centrifuged and digested with trypsin at 37° for 10 minutes. Tissue was centrifuged and resuspended in minimal essential medium with Earle's salt (Invitrogen) containing heat-inactivated fetal bovine serum and horse serum. Cell suspension was passed through cell strainers and plated. After three hours the medium is changed to Neurobasal medium supplemented with B27 MinusAO (Invitrogen). Cultures were maintained for seven days and then immunohistochemical staining was performed to verify the composition of the cultures.

Figure 7:
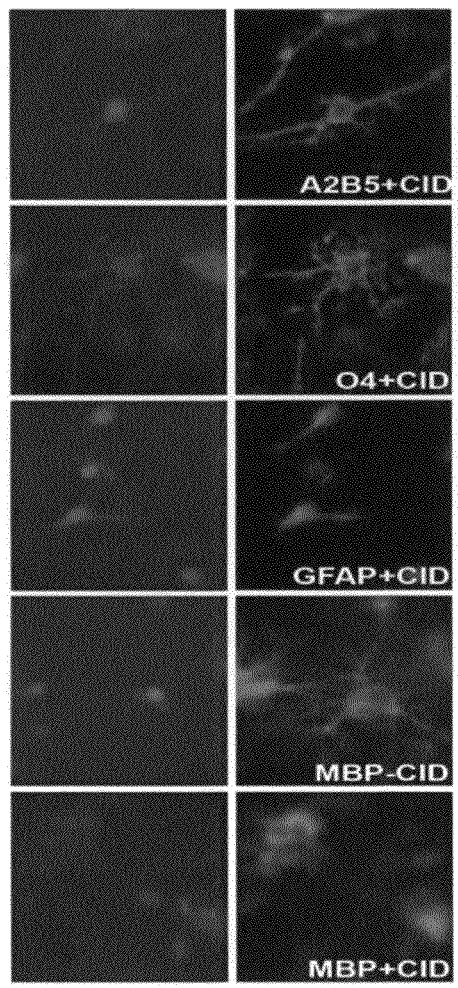
FIG. 7 shows mixed cortical cultures derived from rat pups infected with pLpMBP(iCP9)MG and then exposed to CID. Four hours later cells were stained to identify cell-types. Morphology of MBP+ cells after CID exposure (+CID) was suggestive of apoptosis. Other cells types maintained morphology consistent with a viable cell. This indicates the virus induces cell death in MBP expressing cells.

The mixed primary cortical cultures (consisting of all CNS cell types) were infected with pLpMBP(iCP9)MG and exposed to CID and then analyzed for cell death of oligodendrocytes (MBP+ cells). The MBP promoter was designed to induce cell death only in MBP+ cells, the majority of which are mature oligodendrocytes. Prior to CID expression cells appeared morphologically normal and cell counts of control cultures and virally transfected cultures did not demonstrate significant differences between cell types indicating that viral transfection did not significantly alter the constitution of the culture. After CID exposure MBP-positive, EGFP-positive cells appeared disrupted relative to MBP-positive, EGFP-positive cells not exposed to CID (FIG. 7). Furthermore, A2B5 (oligodendrocytes precursor cells)/EGFP positive cells, GFAP (astrocytes)/EGFP positive cells and O4 positive cells (oligodendrocyte precursor cells)/EGFP positive cells appeared morphologically normal before and after CID exposure.

Figure 8:
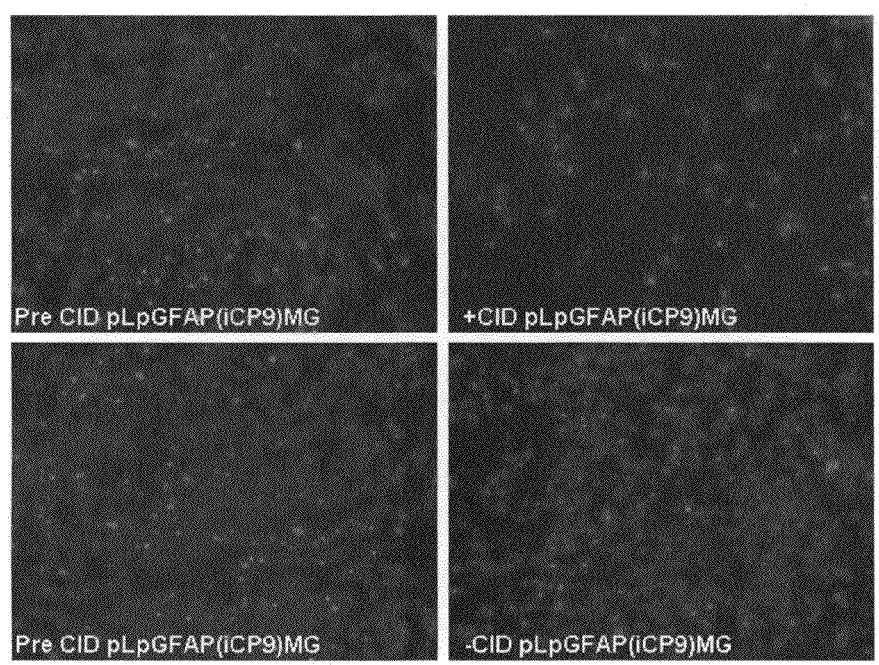
FIG. 8 shows pan purified GFAP+ cells (astrocytes) infected with pLpGFAP(iCP9)MG and exposed to CID (+CID). GFP+ cells underwent apoptosis indicated by the absence of EGFP+ cells four hours after exposure to CID (upper photomicrographs). Parallel cultures not exposed to CID (−CID) maintained a high number of EGFP+ cells (lower photomicrographs).

To test the specificity of the GFAP promoter system, GFAP+ pan purified cultures (cultures of purified astrocytes) were transfected with pLpGFAP(iCP9)MG and exposed to CID. Pan purified GFAP cells infected with pLpGFAP(iCP9)MG were exposed to CID and 4 hours after a decrease in EGFP positive cells was demonstrated while analogous cultures not exposed to CID maintained a high level of EGFP positive cells (FIG. 8). These data confirmed that the GFAP promoter drives iCP9 expression resulting in apoptosis of astrocytes after CID exposure.

Figure 9:
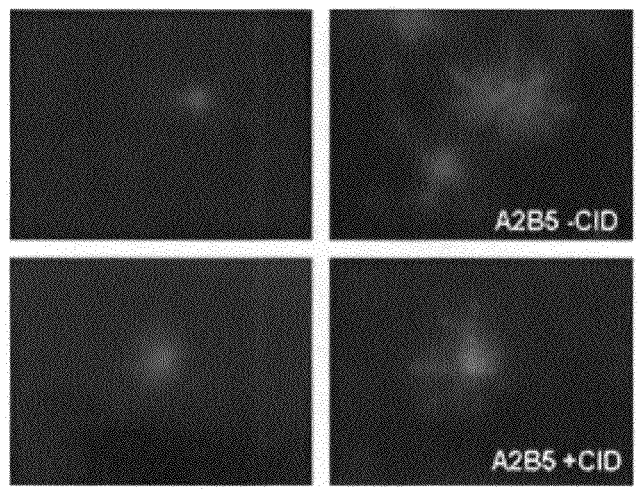
FIG. 9 shows mixed cortical cultures were infected with pLpPDGFR(iCP9)MG virus and exposed to CID (+CID). Four hours later A2B5+ cells were identified undergoing apoptosis based on the loss of viable cell morphology.

To confirm the cell specificity of the PDGFR-α promoter system, rat-derived primary cortical cultures were infected with pLpPDGFR(iCP9)MG virus. In mixed primary cortical cultures (cultures containing all CNS cell types), A2B5-positive cells (A2B5 expression overlaps with PDGFR expression and is used in place of anti-PDDGFR antibody as it is less labor intensive) were identified undergoing apoptosis with altered morphology, while other cell types appear unaffected (FIG. 9). This provides data supporting the oligoprecursor-specificity of the PDGFR-α promoter system.

Example 4

Analysis of Neuronal Response to Acute Insult

Four major classes of responses: apoptosis inducing factors, anti-apoptosis factors, neurotrophic factors and neurotrophic related transcription factors, is analyzed. Analysis of neurotrophic factors is carried out using commercial ELISA assays for GDNF, CNTF, BNDF, NGF, NT-3 and NT 4/5 according to manufacturer's protocol. Twenty-four hour supernatant from mixed cortical cultures are collected after apoptosis at time points described and from mixed cortical cultures that have not been administered the CID, which serve as the control. All samples are run in duplicate and final data represents the mean of the two values.

Analysis of neurotrophic related transcription factors NF-κB and CREB activation are carried out using the Trans-AM P-CREB and NF-κB p65 kits (Active Motif Europe, Rixensart, Belgium) according to manufacturer's instructions. The Trans-Am assays measures the level of the active forms of phosphorylated CREB and NF-κB contained in cell extracts able to bind specifically to oligonucleotide containing the cyclic AMP-response element and the NF-κB consensus site (5'-GGGACTTTCC-3' (SEQ ID NO: 2)) coated to 96-well plates. A secondary horseradish peroxidase-conjugated antibody provides a sensitive colorimetric readout that will be quantified using the ELISA plate reader (BIORAD) at 450 nm. All samples are run in duplicate. Cell extracts are derived from mixed cortical cultures following induced apoptosis at time points defined previously. Control cell extracts consist of mixed cortical cultures not exposed to the CID.

The number of neurons undergoing apoptosis following the loss of oligodendrocytes in mixed cortical cultures is quantified using a TdT-mediated dUTP nick end labeling assay (TUNEL assay, Roche, Indianapolis, Ind.) according to the manufacturer's protocol. The number of positive cells are quantified using microscopy and compared to the number of positive cells in cultures not exposed to the CID. Immunohistochemical (IHC) staining is carried out using anti-FAS and anti-NOS antibodies to quantify expression in neurons from mixed cortical cultures after loss of oligodendrocytes and compared to cultures that have not been exposed to the CID. Staining is conducted using the VECTASTAIN ABC kit (Vector Laboratories Inc., Burlingame, Calif.) per protocol.

Antiapoptotic molecules may play a role in neuronal survival or conversely a decrease in expression may contribute to neuronal loss. A novel factor, E4BP4, appears to play an important antiapoptotic function in neurons in the CNS. Therefore, the level of expression of E4BP4 is examined via immunohistochemistry (IHC) staining in neurons undergoing apoptosis following the loss of oligodendrocytes in mixed cortical cultures and compared to cultures that have not been exposed to the CID. IHC staining is carried out as described above.

Example 5

Identification of Unique Molecules Regulated by Acute Oligodendrocytes

The acute loss and chronic absence of oligodendrocytes represents a unique pathological state in the central nervous system, and therefore, novel genes are upregulated and identified in neurons in response to these events. To detect these genes, a microarray analysis is undertaken. Total RNA is isolated using the RNeasy Mini Kit (Qiagen, Valencia, Calif.) from the remaining culture after induced apoptosis of oligodendrocytes at various time points after the insult. To produce the control array, total RNA is isolated in a similar manner from a culture that has not be exposed to oligodendrocytes death in vitro by withholding the CID. RNA processing and analysis is carried out by the core facility of the Case Western Medical School using standard protocols. Scanned output files will be visually inspected for hybridization artifacts. Arrays are scaled to an average intensity and then analyzed using Affymetrix Microarray 5.0 software. Genes are considered upregulated if the expression is changed >1.5-fold relative to control RNA.

Microarray results are confirmed with immunohistochemical staining of cultures to demonstrate increase expression level if antibodies are available. Where antibodies are not available, quantitative RT-PCR is performed based on the gene sequence to confirm the upregulation of gene expression. Briefly, β-actin serves as baseline gene expression.

Primers are purchased based on cDNA sequence analysis. Real-time PCR is performed using a BioRad iCycler, and the computer calculates the standard curve for the threshold cycle. The mean threshold cycle is calculated from three wells for each sample, and the mean TC and standard curve are used to extrapolate the sample mRNA quantity. In each cell culture mRNA is quantified as a proportion of β-actin mRNA, and the mean proportions from control cultures are compared. Administration of pΔmbpICP9/mEGFP virus to oligodendrocyte precursor cells result in nearly 100% GFP positive cells. The expression of iCP does not occur until oligodendrocytes mature and the administration of the CID results in cell death of oligodendrocytes over 4 to 6 hours based on published data in other cells types (Straathof et al., 2005). Initial analysis of pre-defined pathways such as that to ischemia or hypoxia will be evident in culture neurons in the acute phase after oligodendrocyte loss, as there is most likely a common response to noxious events in neurons. However, the more time that passes from oligodendrocyte loss the response can deviate from known injury response. Furthermore, the microarray analysis of neurons following the loss of oligodendrocytes results in the upregulation and identification of 2 to 4, 2 to 6, or 5 to 10 novel and relevant genes compared to control neurons. Such a profile is identified 72 hours to one week after oligodendrocyte loss, rather then in the acute phase.

Example 6

Animal Model

The virus described above, pΔmbpICP9/mEGFP, which contains the inducible caspase 9 sequence was applied to the CNS of adult rats to create an in vivo model of CNS demyelination. Administration of the viral vector allowed effective transfer of genetic information in a variable area of parenchyma based on the rate of administration (convective distribution) and viral titer. The data demonstrated that areas of the CNS are effectively infected with lentivirus. First, adult Fischer rats were anaesthetized by intraperitoneal injection of ketamine hydrochloride (80 mg/kg) and xylazine (4 mg/ml) and placed in a stereotactic frame. A midline scalp incision is made. Access to brain parenchyma was accomplished by placement of a right-sided burr hole through the skull, at various predetermined coordinates depending on the desired location of the lesion. Lentivirus was administered in serum free media using a sterile 10 μl Hamilton syringe with a No. 32S-gauge needle at a rate dependent upon the target area size (convective distribution of virus is most effective at rates of 0.1 to 0.5 μl/minute). The volume of viral vector (e.g., lentivirus) delivered depends upon the infection efficacy as determined herein and the target area size. After injection, the needle is left in place for five minutes and then slowly withdrawn over the next four minutes. The skin was closed with sutures.

For virus administration to the spinal cord an incision was made in the thoracic spine followed by a lamenectomy to expose the spinal cord. A No. 32S-gauge needle was passed into the posterior column at predetermined coordinates. At various times after injection of virus the CID was administered via intraperitoneal injection, resulting in apoptosis of the infected region of the CNS.

Verification of reversible physiologic dysfunction after acute demyelination. Based on the data a viral vector was utilized to successfully infect areas of the CNS and effectively express transgenes. The physiologic manifestation of acute oligodendrocyte death was initially observed in rats with brain lesions over time. For lesions in the spinal cord a more precise recording mechanism was employed. The functional integrity of axons in the dorsal columns is examined in vivo using somatosensory evoked potential recordings (SSEP).

At various time points after the administration of the CID rats were anesthetized as described previously for SSEP recording. SSEPs were recorded from a screw electrode over the right somatosensory cortex referenced to an Ag/AgCl disk electrode placed under the hard plate while the contralateral sciatic nerve is stimulated at 1 Hz (0.2 ms pulse duration and 40 mA constant current intensity for an average of 200 sweeps). A ground electrode was placed on the scalp transdermally. SSEP amplitude is measured from the first negative peak to the positive peak. Response latency was measured as the time between the onset of stimulus and the first peak. The amplitude and latency values was recorded as the mean of three independent measures. These measures were repeated at 1, 2, 7 and 14 days after the administration of the CID to establish a measurable pattern of CNS damage and repair. Immunohistochemical analysis of acute lesions. In order to evaluate the cellular changes associated with iCP9 oligodendrocyte cell death, animals were sacrificed at various time points following the administration of the CID.

Rat brains or spinal cords were snap frozen in isopentane for 20 seconds and then stored at −80° C. until sectioning. Coronal thin sections of the brain and axial sections of the spinal cord at 10-μm thickness were generated using a cryostat (−20° C.). Initially this was conducted at 1-day post death to determine the success of CID induced cell death. Afterwards, 1, 2, 7 and 14-day post CID animals were sacrificed and examined using fluorescent microscopy, luxol fast blue staining and hematoxylin and eosin (H&E) staining. Thin section of brain and cord were examined via immunohistochemical staining using various antibodies to determine the extent of inflammation (anti-LCA antibody, anti-ED1) and gliosis (anti-GFAP antibody) that has occurred.

The photograph in FIG. 2 demonstrates that concentrated lentivirus can be applied directly to the CNS and the extent and area of infection can be determined based on the number of GFP positive cells detected after sacrifice in thin sections of the brain or spinal cord. This data establishes the transfer mechanism for specific cell death in vitro and in vivo that is the basis of the model proposed herein.

Example 7

Identification of Axonal Transaction and Neuronal Apoptosis in Acute Lesions

Thin sections are used to detect focal neuron damage at the site of the lesion in the form of transected axons or apoptotic neurons. Immunohistochemical staining is conducted on thin sections encompassing demyelinating lesions using anti-amyloid precursor protein (APP) antibody. This identifies disturbances of axonal transport and transection as APP accumulates at the ends of such axons. Similarly, Bielschowskys silver impregnation staining is utilized to detect neurons and transected axons. Fixed sections are stained in prewarmed (40° C.) 10% silver nitrate for ten minutes and then washed in PBS. Ammonium hydroxide is added to the silver nitrate solution and slides incubated for 30 minutes at 40° C. after which time slides will be placed directly in developer working solution (40% formaldehyde, citric acid, nitric acid solution) for one minute.

The reaction is halted in 1% ammonium hydroxide, washed in PBS and then incubated in 5% sodium thiosulfate for 5 minutes. Finally, slides are dehydrated and mounted.

Using this staining technique, transected axons can be identified and the number of axons are counted and compared to control animals that have been infected with virus but have not been administered the CID and therefore do not have focal areas of demyelination. Neurons are counted in and surrounding acute lesions at various time points after cell death and compared to thin sections derived from animals that have received virus but not CID and therefore do not have focal areas of demyelination. A 0.01 mm$^2$ field, defined by an ocular morphometric grid, taken throughout the middle of each lesion area or a distant, normal area are selected for examination. In this field APP positive fibers or Bielschowskys silver impregnated fibers are counted under a 100× objective.

Example 8

Identification of Distant Neuronal Loss after Acute Demyelinating Lesions

In order to determine whether demyelination in the CNS can result in the death of distant neurons with axons transversing the lesion, neurons are examined in the contralateral red nucleus following the production of demyelinating lesions in the lateral fasiculus of the spinal cord at various time points. The number of neurons in the red nucleus of rats after the induction of oligodendrocyte death in the spinal cord are compared to the number in the red nucleus of rats infected with virus that have not received the CID. Also, a TdT-mediated dUTP nick end-labeling assay (TUNEL assay, Roche, Indianapolis, Ind.) is utilized to detect apoptotic activity. This is conducted on thin sections according to the manufacturer's protocol. Subcortical Lesion Burden and Spinal Cord Atrophy. Extensive spinal cord atrophy is a well defined feature of MS. Demyelinating events in distant areas of the CNS induce spinal cord atrophy and that this induction is related to the extent of demyelinating burden is determined.

Therefore, as described previously a viral vector (e.g., iCP9), is delivered to subcortical regions of the CNS and delivery of the CID results in areas of demyelination. Eight months after the original insult rats are sacrificed, spinal cord removed, snap frozen, thin sections prepared and H&E stained. Spinal cord diameter is measured and compared to control animals that are infected in the same manner with the iCP9 virus, but will not have received the CID and therefore, will not have acute demyelinating lesions. The number of lesions, location, as well as the time interval between lesions can all be varied to produce greater degrees of demyelinating area and frequency to maximize the possibility of detecting atrophy in the spinal cord.

Finally, results identify changes in survival or apoptotic factors or unique genes are verified using the in vivo model. This is carried out using immunohistochemical staining. Results can also be assayed in the in vivo model, which provides another physiologic substrate to study neuronal response to demyelination. The acute loss of oligodendrocytes in the spinal cord can result in an acute physiological dysfunction and measurable changes in SSEP recordings. Specifically, an attenuation of amplitude and increase in latency are identified. This corrects to baseline over a time course that are determined as the rat recovers from the initial insult. Using Luxol Fast Blue staining after cell death, an area of acute demyelination is defined. The extent and type of inflammatory infiltrate is determined using immunohistochemical staining.

Thus, a mild nonspecific inflammatory infiltrate can ensue and dissipate over several weeks. As has been demonstrated in pathological specimens from MS patients, transected axons are localized within the acute lesion. Finally, a decrease in the number of viable neurons in the red nucleus after the induction of multiple, distant demyelinating lesions are observed. The time course and extent of loss can occur slowly over time, e.g., may be identified from about 6 to 12 months after demyelination.

Example 9

Transgenic Animal Expressing Caspase-9

A transgenic mouse expressing caspase-9 under the control of myelin basic promoter is created by first generating a transgenic targeting vector construct. Various nucleic acid elements are incorporated to ensure the expression of caspase-9 in mouse. A synthetic intronic element is placed in front of caspase-9 cDNA for proper processing of pre-mRNA originated from the vector. A poly adenylation signal is incorporated at the end of caspase-9 cDNA for proper processing of mRNA. To allow inducible expression of caspase-9, a stop codon floxed by two LoxP sites (Cre-recombinase recognition sites) are incorporated between the myelin basic promoter and the synthetic intron. The vector is linearized for efficient integration of the vector into the genome and injected into a number of pronuclei by microinjection. The injected pronuclei are implanted into pseudopregnant FVB/N strain mice. The pups are screened for the integration of the injected vector(s) into the host genome. Pups positively identified in the screen are weaned and mated with a transgenic mice containing ER-Cre transgene. The pups from the mating are screened for animals harboring both the caspase-9 and ER-Cre transgenes. Tamoxifen is peritoneally injected to induce the expression of Cre protein from ER-Cre transgene. The excision of LoxP site and the resulting expression of caspase-9 in myelin sheath are confirmed in an immunofluorescence staining using anti-caspase-9 antibody.

Example 10

Cell Specific Induction of Apoptosis In Vivo

Figure 10:
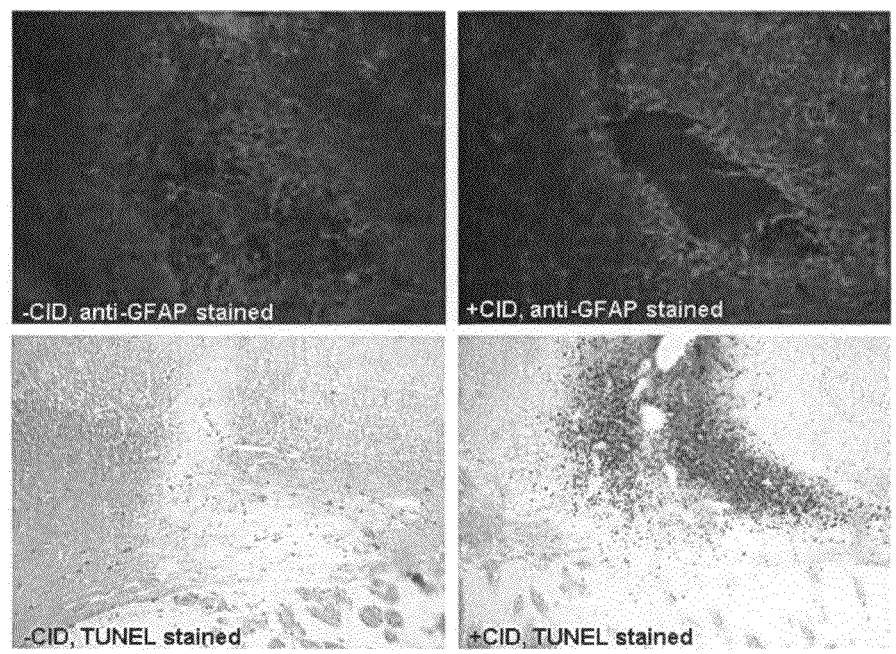
FIG. 10 shows results from injection of pLpGFAP(iCP9) MG virus into the corpus callosum of rats. Twenty-four hours after exposure to CID apoptosis is identified at the site of infection with a loss of GFAP+ cells (Right panels). However, infection followed by exposure to vehicle failed to generate apoptosis or loss GFAP+ cells (left Panels). This suggests that the virus results in the specific loss of GFAP+ cells (astrocytes) via apoptosis.

The system was tested in vivo to ensure that cell specific apoptosis could be induced and the timing of cell ablation controlled as it was in vitro. To this end, virus was injected into the corpus callosum of adult Fischer rats and then three weeks later CID was administered into the ipsilateral ventricle. Rats were sacrificed 24-hours thereafter, brains removed in whole, fixed and cyrosectioned for analysis. Rats injected with pLpGFAP(iCP9)MG (GFAP promoter limits expression to astrocytes) and then CID were sacrificed 24-hours later and demonstrated TUNEL positive staining at the site of virus infection (demarcated by EGFP positive cells as the vector results in constitutive expression of EGFP). The TUNEL (TdT-mediated dUTP-X nick end-labeling) system adds a tag on to DNA that has been fragmented during the apoptosis cascade allowing for labeling using standard immunohistochemistry. Thin sections derived from control rats receiving glycerol rather than CID were TUNEL negative. Consecutive thin sections were then stained with anti-GFAP antibody to identify astrocytes. GFAP+ cells were not detected at the area of viral infection in thin sections derived from rats administered CID, in contrast to sections derived from control rats receiving glycerol (FIG. 10). This confirmed that in vivo the iCP9 system induces apoptosis only after CID administration and effectively ablates GFAP+ astrocytes.

Figure 11:
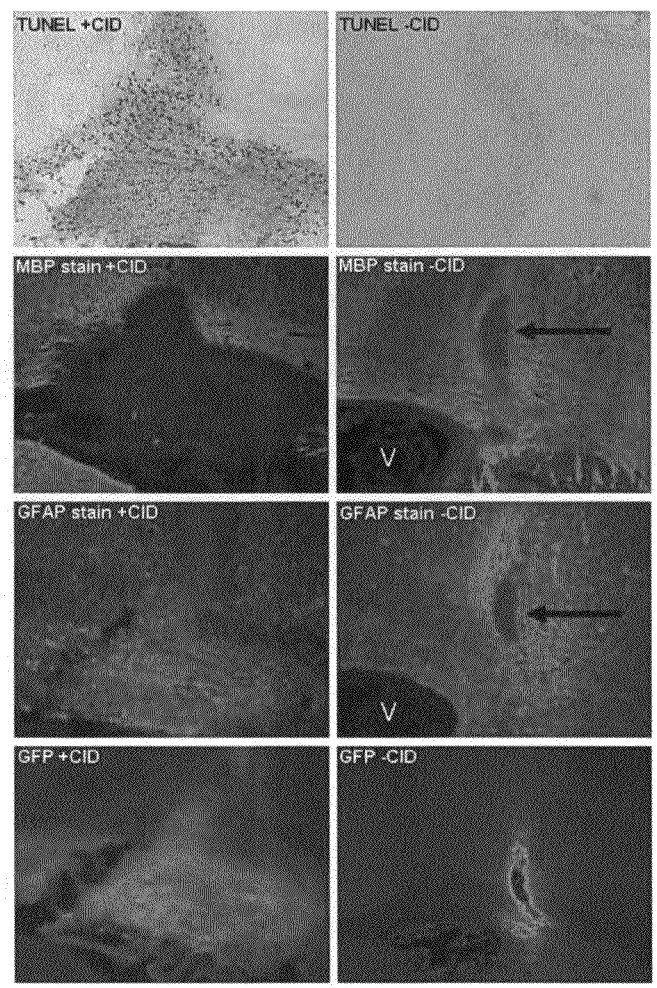
FIG. 11 shows pLpMBP(iCP9)MG virus injected into the corpus callosum of rats to specifically ablate oligodendrocytes. Twenty-four hours after exposure to CID (CID+) apoptosis was identified at the site of infection via TUNEL stain (top panels) and the absence of MBP staining cells (second row). The area that fails to stain with anti-MBP antibody, stains positive with anti-GFAP antibody indicating that cells persist in that area. The area indicated by black arrows stains negative for both and represents a tissue defect created by the needle insertion. V=ventricle. The bottom panel show the extent of infection as all infected cells are GFP+.

In a similar manner, rats injected with pLpMBP(iCP9)MG (designed to ablate oligodendrocytes) and exposed to CID failed to stain with anti-MBP antibody at the site of infection, while thin sections from control rats infected with pLpMBP (iCP9)MG and administered glycerol appeared normal after immunohistochemical staining using anti-MBP antibody. TUNEL positive cells were identified at the site of infection after exposure to CID, but not in controls exposed only to glycerol (FIG. 11).

These data confirmed that the iCP9 system is able to induce apoptosis in vivo in a time controlled fashion and appears specific to cell-type based on the promoter sequence utilized.

Example 11

Cellular Response to Acute Oligodendrocyte Apoptosis in the CNS

The demyelinating and repair process in rats both in the spinal cord and the brain is defined by using rat pups, 3 days old (P3), that are anesthetized by intraperitoneal injection of ketamine hydrochloride (80 mg/kg), acepromazine (2.1 mg/kg), and xylazine (4 mg/ml) and placed in a stereotactic frame (Stoelting Co). A 10 µl Hamilton syringe with a No. 26S-gauge needle is passed through the soft skull 0.5 mm anterior and 0.5 mm lateral of bregma at a depth of 0.2 mm. Five microliters of pLpMBP(iCP9)MG virus (selectively ablates oligodendrocytes) in serum free media is injected using a 10 µl Hamilton syringe with a No. 26S-gauge needle at a rate of 2 µl/min. For rats receiving injections into the thoracic spinal cord, a 10 µl Hamilton syringe with a No. 26S-gauge needle is manually passed through the spinal cord. Virus is then injected at the same rate as in brain by way of a microinjection system (Harvard Co). After injection, the needle is be left in place for five minutes and then slowly withdrawn over the next four minutes.

Three weeks after injection of the virus, 5 µA of CID (10 nm) is injected into the ipsilateral ventricle (−0.8 mm anterior and 1.4 mm lateral to bregma at a depth of 3.6 mm) which results in the apoptosis of infected oligodendrocytes. Every other day, beginning on the day of CID injection, animals receive an intraperitoneal injection of 100 mg/kg BrdU labeling mix (Sigma) which incorporates into proliferating cells and allows for their identification using immunohistochemistry. Rats are sacrificed at days 1, 7, 14, 21 and 28 post-CID.

Control rats are injected with virus in the same manner as the experimental animals but receive an injection of glycerol (CID is diluted in glycerol) rather than CID. Rats are deeply anesthetized and perfused transcardially first with 150 ml of 0.9% NaCl saline solution followed by equal volume of ice-cold 4% paraformaldehyde. Whole brain and/or spinal cord is then removed and post-fixed in paraformaldehyde for at least 4 hours followed by cryoprotection in 30% sucrose until tissue sinks to the bottom of the container. Samples are then frozen in OCT and cryosectioned at 10 to 20 µm on superfrost plus slides. This experiment is repeated in the spinal cord in the same manner.

Immunohistochemistry. Tissue derived from 1, 7, 14, 21 and 28 day post-CID animals is examined using fluorescent microscopy to identify the area of infection. In order to define the area of acute demyelination and subsequent remyelination, black gold staining of myelin is conducted on thin sections after the induction of acute oligodendrocyte death at each time point. The time to demyelination in this experiment is defined as the time point at which the area of infection does not stain with black gold, and the time to remyelination in this experiment is defined as the time point after demyelination that black gold stains the area of infection with equal intensity as the neighboring unaffected myelin, is noted for each animal and a mean and standard deviation calculated. These data is compared to the time to demyelination and the time to remyelination for control animals. Statistical analysis is not conducted as the control is not expected to demyelinate/remyelinate. However, these data points serve as controls for future experiments.

Thin sections of brain and/or spinal cord is examined to determine the extent of inflammation using anti-CD45 antibody (T and B cells), anti-ED1 antibody (microglial cells), anti-CD68 antibody (macrophages) and gliosis using anti-GFAP antibody (astrocytes). This is done at each time point and qualitatively compared to labeled thin sections derived from equivalent control animals.

Sections are also stained with anti-nestin antibody (pluripotent stem cell), anti-NG2+ antibody (glial committed stem cell), anti-PDGFR-alpha (total pool of OPCs), anti-O4+ antibody (early OPC lineage when O1 negative), anti-O1 antibody (late OPC lineage) and anti-MBP antibody (mature oligodendrocyte) to identify stem cell and oligodendrocyte precursor cell mobilization and incorporation into the dynamic lesion site. These antibodies identify different cells along the pathway from CNS stem cell to mature oligodendrocyte. Thin sections are then examined using fluorescent microscopy and labeled cells counted in a 0.01 $mm^2$ field defined by an ocular morphometric grid under a 100× objective. Four distinct locations within the lesion are randomly selected and counted and an average cell number and standard deviation for each section at each time point will be calculated. This is compared to the corresponding site in the contralateral hemisphere, which does not have a demyelinating lesion and to control animals which were infected with virus but did not receive CID and therefore should not have a demyelinating lesion. The area for counting in the control animal is the site of viral injection identified by the presence of EGFP+ cells. The average cell count for each area is compared using a paired t-test. This is repeated for each antibody used at each time point to determine which oligodendrocyte subtype migrates to the lesion and the temporal distribution of this migration.

Rats are injected with BrdU labeling mix after CID exposure. BrdU incorporates into the DNA of cells during division and allows for the identification of cells that divided by the application of anti-BrdU antibody and standard immunohistochemistry. After completion of staining for cell types, thin sections are labeled with anti-BrdU antibody with a secondary antibody distinct from that used in the initial labeling procedure. The overlap of signals identify the proliferating cell types. The double stained sections are compared to control sections at analogous time points. If the same proliferating cell type is identified in the control sections then double stained cells are counted in the entire ipsilateral hemisphere of four sections and averaged and compared to average counts derived from control sections which can then be statistically compared using a standard t-test. If double labeled cells are absent in controls the quantitative measure is presence or absence of the double labeled cells.

The above experiments are also carried out in the spinal cord with comparable controls that receive viral injection into the spinal cord but vehicle (glycerol) rather than CID. The preparation of animals for spinal cord demyelination differs in that the CID is injected into the cisterna magna rather than the ipsilateral ventricle. This is accomplished by palpation along the spinal cord to the base of the skull followed by passage of the Hamilton syringe into this space.

Example 12

The Response of Neurons to the Acute Loss of Oligodendrocyte In Vivo

Identification of axonal transection in acute lesions. Demyelinating lesions are produced as describe in Example 11. Animals are sacrificed at time points determined by data from Example 11. Control rats are injected with virus in the same manner as the experimental animals but receive an injection of glycerol (CID is diluted in glycerol) rather than CID. Rats are sacrificed and prepared as described. In order to characterize the response of axons within the lesion, thin sections are labelled with anti-neurofilament (NF) antibody and anti-amyloid precursor protein (APP). The former identifies axons in the lesion while the later identifies disturbances of axonal transport and transection. NF+ axons and APP positive axons are counted using a 0.01 mm$^2$ field defined by an ocular morphometric grid are counted under a 100× objective. Four distinct areas within the demyelinated lesions are counted and averaged.

A percentage of transected axons (APP+) is calculated by dividing the average APP+ cell count by the mean number of axons in the lesion (NF+). These data is compared to control animal counts conducted at the site of infection in a comparable manner. Counting of neurons is conducted at days 1, 7, 14, 21 and 28 post-CID. A simple t-test is used to determine statistical significance between control and experimental counts at any given time point.

Identification of distant neuronal loss after acute demyelinating lesions. In order to determine whether demyelination in the CNS can result in the loss of neurons in spatially distinct regions of the CNS, neurons are examined in the substantia nigra following the induction of a demyelinating lesion in the lower thoracic spinal cord. Rats are prepared as described but the site of the lesion is the thoracic spinal cord and CID is injected into the cisterna magna as described previously. Controls rats are injected with virus but receive a glycerol injection into the cisterna magna rather than CID. Rats are sacrificed at the same time points (1, 7, 14, 21 and 28 days) and whole brain and spinal cord removed and prepared as described. The spinal cord is sectioned and stained with black gold to confirm the presence of a demyelinating lesion. Brain sections incorporating the substantia nigra, identified by its anatomical location and appearance, is labeled with anti-NF1 antibody and neurons counted as described above. The average number of neurons in the substantia nigra of rats after the induction of oligodendrocyte death in the spinal cord is compared to the average number in the substantia nigra of control rats which do not have a demyelinating lesion. Similarly, a TUNEL stain is performed on thin sections of the brain that encompass the substantia nigra derived from rats with demyelinating lesions in the spinal cord to detect active apoptosis of neurons. The TUNEL (TdT-mediated dUTP-X nick end-labeling) system adds a tag onto DNA that has been fragmented during the apoptosis cascade allowing for labeling using standard immunohistochemistry. If TUNEL positive cells are identified within the substantia nigra they are counted. As before the TUNEL stain results are compared to staining and counts in the substantia nigra of control rats and average counts compared with a t-test. These experiments determine if distant loss of oligodendrocytes effects the survival of unrelated neurons in the CNS.

Determination of the relationship between demyelinating burden and neuron loss. The loss of distant axons in normal appearing brain may be dependant on the extent of demyelination in the CNS. To test this, the size of demyelinating lesions and the number of demyelinating lesions is altered. P3 rats are injected with virus in the thoracic spinal cord and into the bilateral corpus callosum. Rats are allowed to mature and at P20 rats are injected with CID as described. Rats are sacrificed at day 28 post CID injection and tissue from the brain and spinal cord prepared as described above. The time point for analysis may vary, but is completed after the lesions remyelinate. Control rats receive the identical viral injections but receive glycerol rather than CID at P20. As described above, after lesion induction, which is multifocal in this example, the integrity of neurons in the substantia nigra is examined via TUNEL assay and neuron counting. The number of viable neurons and apoptotic cells per 0.01 mm$^2$ field defined by an ocular morphometric grid under a 100× objective is averaged from 4 separate fields within the substanta nigra in the same section and compared to control animals counted in the same manner. Cell counts are compared using a standard t-test.

Verification of reversible physiologic dysfunction after acute demyelination. The functional integrity of axons in the dorsal columns is examined in vivo using somatosensory evoked potential recordings (SSEP). At various time points after the administration of the CID rats are anesthetized as described previously. SSEPs are recorded from an electrode inserted into the spinal cord above the lesion referenced to an Ag/AgCl disk electrode placed under the hard plate while the contralateral sciatic nerve is stimulated at 1 Hz (0.2 ms pulse duration and 40 mA constant current intensity for an average of 200 sweeps). A ground electrode is placed on the scalp transdermally. SSEP amplitude is measured from the first negative peak to the positive peak. Response latency is measured as the time between the onset of stimulus and the first peak. The amplitude and latency values are recorded as the mean of three independent measures. These data is collected at time points, but also includes a baseline prior to demyelination, a data point after demyelination and one after repair has occurred histological. The control data is obtained by recording from the controlateral dorsal columns in the same rat. The mean amplitude and latency value from the lesion side (experimental side) is compared to the contralateral dorsal column (control side) using a standard t-test.

Example 13

The Role of Oligodendrocyte Precursor Cells in the Remyelination Process in the Adult Rat To selectively ablate OPCs, a novel viral vector was created using vector strategies described. Based on cell morphology changes, that A2B5 labeled cells undergo apoptosis after infection with the pLpPDGFR(iCP9)MG and CID exposure as described above. Pan purified A2B5+ cells (culture enriched with A2B5+ by capturing cells with antibodies) and P3 derived mixed cortical cultures (methods to describe cultures described earlier) cultures grown in parallel are infected but not exposed to CID and serve as a control for labeling and ELISA studies. Both sets of cultures are stained with anti-A2B5 antibody and TUNEL stain to determine the specificity of cell ablation. A2B5 expression overlaps with PDGFR-α expression and is easier to label in vitro and therefore serves as a surrogate marker of PDGFR-α+ cells. Mixed cortical cultures are also stained with anti-GFAP (astrocyte label) and anti-MBP (oligodendrocytes label) to ensure that other cells types are not affected by infection with this viral construct. The pan-purified A2B5+ cell cultures are exposed to serial dilutions of pLpPDGFR(iCP9)MG virus and exposed to CID. Cultures are then subjected to the Cell Death Detection Elisa Plus (Roche Inc) system according to manufacturer protocols (described in preliminary work) in order to quantify apoptosis levels. This confirms that PDGFR+ cells are the only cells ablated after infection and CID exposure. All cultures are then run in triplicate to ensure reproducibility.

Upon confirmation of efficacy and specificity, the pLpPDGFR(iCP9)MG virus will be injected into P3 rat brains or thoracic spinal cord. Animals will be allowed to mature and at age P30 lysolethicin will be injected into the ipsilateral corpus collosum, at the site of original virus infection. Lysolethicin (LPC) is a detergent that will result in rapid cell membrane destruction and acute loss of myelin with axon preservation. Twenty-four hours after LPC is injected into the rat brain, animals will be sacrificed to confirm that the experimental procedure has resulted in the expected in vivo paradigm. The presence of a LPC induced demyelinating lesion within the area of original pLpPDGFR(iCP9)MG infection will be confirmed by identifying the area of viral infection on thin sections using fluorescent microscopy. Subsequently, sections with EGFP+ cells will be stained with black gold to confirm the presence of a superimposed demyelinating lesion. I propose the use of 4 animals to confirm that I am able to reproducibly create a LPC lesion within the area of original viral injection. There is no control and no statistical analysis for this experiment.

Once the position of infection and demyelination are confirmed, the experiment is repeated with the addition of CID to ablate PDGFR+ OPCs 24 hours after the injection of LPC. Animals are sacrificed at days 1, 7, 14, 21 and 28 to determine the effect of OPC ablation on myelin repair. The controls for these studies are animals infected with pLpPDGFR(iCP9)MG virus at P3 with a superimposed LPC lesion at P30 but receive glycerol rather then CID thereafter. Therefore they should have a demyelinating LPC induced lesion but no OPC ablation and should repair in a pre-defined manner.

Animals with superimposed LPC demyelinating lesions and subsequent OPC ablation (experimental group) are compared to animals with superimposed LPC lesions and no OPC ablation (control group) using the time to remyelinate data point identified with black gold staining (see Example 11). Furthermore, the time required for OPC migration to the site of LPC lesion is also recorded and compared between groups. Both the time to remyelinate and the time to OPC migration is recorded for each animal and statistical means of each group compared using standard t-test analysis. As described in Example 11, sections are stained for the presence of oligodendrocyte cell types, astrocytes and inflammatory cells. Cells are counted on labeled sections per the protocol described in Example 11 and means calculated and compared to the average cell counts in control groups using a standard t-test.

Finally, injecting all animals with BrdU every other day after CID allows for the identification of proliferating cells as described. After completion of staining for cell types, thin sections are then labeled with anti-BrdU antibody with a secondary antibody distinct from that used in the initial labeling procedure. The overlap of signals identifies the proliferating cell types. The double stained sections are compared to control sections at analogous time points. If the same proliferating cell type is identified in the control sections then double stained cells are counted in the entire ipsilateral hemisphere of four sections and averaged and compared to average counts derived from control sections which can then be statistically compared using a standard t-test. If double labeled cells are different than those identified in control animals there is no quantification.

This experiment can be repeated in the spinal cord.

The present invention is not limited to the embodiments described above, but is capable of modification within the scope of the appended claims. Those skilled in the art will recognize, or be able to ascertain using no more than routine experimentation, many equivalents of the specific embodiments of the invention described herein.

What is claimed is:

1. A method of screening for a biologically active agent that modulates a phenomenon associated with a demyelination or blood brain barrier disorder comprising:
   a) administering a candidate agent to a non-human transgenic animal, wherein said phenomenon occurs in said animal upon expression of a nucleic acid sequence encoding a cell death mediator protein (CDMP); wherein said nucleic acid sequence expression is regulated by a cell-specific expression regulatory element;
   b) activating said CDMP to effect apoptosis in at least one cell in said animal, wherein said cell is associated with a demyelination blood brain barrier disorder; and,
   c) detecting an effect of said agent upon said phenomenon, wherein said CDMP is selected from the group consisting of caspase 2, caspase 5, caspase 8, caspase 9, caspase 10, and caspase 11.

2. The method of claim 1, wherein after step b), said animal is allowed to recover from said phenomenon.

3. The method of claim 1, wherein said phenomenon is characterized by a loss of oligodendrocytes, astrocytes, pericytes, or Schwann cells in said animal.

4. The method of claim 1, wherein said phenomenon is characterized by a decrease in myelinated axons or an increase in blood brain barrier permeability.

5. The method of claim 1, wherein said regulatory element is from a gene selected from the group consisting of CC1, myelin basic protein (MBP), ceramide galactosyltransferase (CGT), oligodendrocyte-myelin glycoprotein (OMG), cyclic nucleotide phosphodiesterase (CNP), NOGO, myelin protein zero (MPZ), peripheral myelin protein 22 (PMP22), protein 2 (P2), GFAP, AQP4, PDGFα, RG5, pGlycoprotein, neurturin (NRTN), artemin (ARTN), persephin (PSPN), sulfatide, PDGFR-β, PDGFR-α, and proteolipid protein (PLP) gene.

6. The method of claim 1, wherein said demyelination disorder is multiple sclerosis.

7. The method of claim 1, wherein said detecting an effect involves a PCR assay, an immunoassay, a hybridization assay or a combination thereof.

8. The method of claim 1, wherein said candidate agent is an antisense oligonucleotide, a peptide, an antibody, a liposome, a small interfering RNA, a small organic compound, or an inorganic compound.

9. The method of claim 1, wherein said at least one cell is a neuronal, glial or mural cell.

10. The method of claim 9, wherein said at least one cell is an oligodendrocyte, astrocyte, microglial cell, pericyte, or Schwann cell.

11. The method of claim 1, wherein said CDMP is a chimeric protein comprising a binding domain for an FK506-type ligand, an FKBP12-type ligand, a cyclosporin A-type ligand, tetracycline or a steroid ligand.

12. The method of claim 1, wherein expression of said CDMP is inducible.

13. The method of claim 1, wherein the apoptosis promoting activity of said CDMP is inducible.

14. The method of claim 13, wherein said activity is induced by a chemical inducer of dimerization (CID).

15. The method of claim 1, wherein said CDMP is an inducible caspase 9 (iCP9).

16. The method of claim 15, wherein said CID is AP20187.

17. The method of claim 1, wherein apoptosis is induced in a post-mitotic cell.

18. The method of claim 1, wherein the effect of said agent is to enhance remyelination.

19. The method of claim 18, wherein enhancement of remyelination is determined by increased expression of a myelin-specific marker protein.

20. The method of claim 19, wherein said myelin specific marker protein is selected from the group consisting of CC1, myelin basic protein (MBP), ceramide galactosyltransferase (CGT), myelin associated glycoprotein (MAG), myelin oligodendrocyte glycoprotein (MOG), oligodendrocyte-myelin glycoprotein (OMG), cyclic nucleotide phosphodiesterase (CNP), NOGO, myelin protein zero (MPZ), peripheral myelin protein 22 (PMP22), protein 2 (P2), galactocerebroside (GalC), sulfatide, PDGFR-β, PDGFR-α PDGF-α, proteolipid protein (PLP), and combinations thereof.

21. The method of claim 1, wherein said CDMP is selected from the group consisting of caspase 2, caspase 5, caspase 8, caspase 10, and caspase 11.

22. The method of claim 1, wherein said CDMP is caspase 9.

23. The method of claim 1, wherein said CDMP is a chimeric protein comprising a binding domain for a cyclosporin A-type ligand, tetracycline or a steroid ligand.

24. The method of claim 1, wherein said CDMP is a chimeric protein comprising a binding domain for an FK506-type ligand or an FKBP12-type ligand.

25. The method of claim 21, wherein after step b), said animal is allowed to recover from said phenomenon.

26. The method of claim 21, wherein said phenomenon is characterized by a loss of oligodendrocytes, astrocytes, pericytes, or Schwann cells in said animal.

27. The method of claim 21, wherein said phenomenon is characterized by a decrease in myelinated axons or an increase in blood brain barrier permeability.

28. The method of claim 21, wherein said regulatory element is from a gene selected from the group consisting of CC1, myelin basic protein (MBP), ceramide galactosyltransferase (CGT), oligodendrocyte-myelin glycoprotein (OMG), cyclic nucleotide phosphodiesterase (CNP), NOGO, myelin protein zero (MPZ), peripheral myelin protein 22 (PMP22), protein 2 (P2), GFAP, AQP4, PDGFα, RG5, pGlycoprotein, neurturin (NRTN), artemin (ARTN), persephin (PSPN), sulfatide, PDGFR-β, PDGFR-α, and proteolipid protein (PLP) gene.

29. The method of claim 21, wherein said demyelination disorder is multiple sclerosis.

30. The method of claim 21, wherein said detecting an effect involves a PCR assay, an immunoassay, a hybridization assay or a combination thereof.

31. The method of claim 21, wherein said candidate agent is an antisense oligonucleotide, a peptide, an antibody, a liposome, a small interfering RNA, a small organic compound, or an inorganic compound.

32. The method of claim 21, wherein said at least one cell is a neuronal, glial or mural cell.

33. The method of claim 32, wherein said at least one cell is an oligodendrocyte, astrocyte, microglial cell, pericyte, or Schwann cell.

34. The method of claim 21, wherein said CDMP is a chimeric protein comprising a binding domain for an FK506-type ligand, an FKBP12-type ligand, a cyclosporin A-type ligand, tetracycline or a steroid ligand.

35. The method of claim 21, wherein expression of said CDMP is inducible.

36. The method of claim 21, wherein the apoptosis promoting activity of said CDMP is inducible.

37. The method of claim 36, wherein said activity is induced by a chemical inducer of dimerization (CID).

38. The method of claim 37, wherein said CID is AP20187.

39. The method of claim 21, wherein apoptosis is induced in a post-mitotic cell.

40. The method of claim 21, wherein the effect of said agent is to enhance remyelination.

41. The method of claim 40, wherein enhancement of remyelination is determined by increased expression of a myelin-specific marker protein.

42. The method of claim 41, wherein said myelin specific marker protein is selected from the group consisting of CC1, myelin basic protein (MBP), ceramide galactosyltransferase (CGT), myelin associated glycoprotein (MAG), myelin oligodendrocyte glycoprotein (MOG), oligodendrocyte-myelin glycoprotein (OMG), cyclic nucleotide phosphodiesterase (CNP), NOGO, myelin protein zero (MPZ), peripheral myelin protein 22 (PMP22), protein 2 (P2), galactocerebroside (GalC), sulfatide, PDGFR-β, PDGFR-α PDGF-α, proteolipid protein (PLP), and combinations thereof.

* * * * *

SEQUENCE LISTING

```
<160> NUMBER OF SEQ ID NOS: 2

<210> SEQ ID NO 1
<211> LENGTH: 4
<212> TYPE: PRT
<213> ORGANISM: Unknown
<220> FEATURE:
<223> OTHER INFORMATION: Description of Unknown: Endoplasmic reticulum
      retention sequence

<400> SEQUENCE: 1

Lys Asp Glu Leu
1

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gggactttcc                                                          10
```